US009034635B2

(12) United States Patent
Termaat et al.

(10) Patent No.: US 9,034,635 B2
(45) Date of Patent: May 19, 2015

(54) THERMOCYCLER AND SAMPLE VESSEL FOR RAPID AMPLIFICATION OF DNA

(75) Inventors: Joel R. Termaat, Lincoln, NE (US); Hendrik J. Viljoen, Lincoln, NE (US); Scott E. Whitney, Lincoln, NE (US)

(73) Assignee: Streck, Inc., Lavista, NE (US)

( * ) Notice: Subject to any disclaimer, the term of this patent is extended or adjusted under 35 U.S.C. 154(b) by 677 days.

(21) Appl. No.: 12/918,594

(22) PCT Filed: Feb. 19, 2009

(86) PCT No.: PCT/US2009/034446

§ 371 (c)(1), (2), (4) Date: Oct. 27, 2010

(87) PCT Pub. No.: WO2009/105499

PCT Pub. Date: Aug. 27, 2009

(65) Prior Publication Data

US 2011/0039305 A1 Feb. 17, 2011

Related U.S. Application Data

(60) Provisional application No. 61/066,365, filed on Feb. 20, 2008.

(51) Int. Cl.

| | |
|---|---|
| ***C12P 19/34*** | (2006.01) |
| ***B01L 7/00*** | (2006.01) |
| *B01L 3/00* | (2006.01) |

(52) U.S. Cl.

CPC .. *B01L 7/52* (2013.01); *B01L 3/505* (2013.01); *B01L 2300/043* (2013.01); *B01L 2300/0838* (2013.01); *B01L 2300/1822* (2013.01)

(58) Field of Classification Search

None

See application file for complete search history.

(56) References Cited

U.S. PATENT DOCUMENTS

| | | | |
|---|---|---|---|
| 3,722,502 | A | 3/1973 | Besuner et al. |
| 3,911,918 | A | 10/1975 | Turner |
| 4,683,202 | A | 7/1987 | Mullis |
| 4,900,321 | A | 2/1990 | Kaufman et al. |
| 4,902,624 | A | 2/1990 | Columbus et al. |
| D313,098 | S | 12/1990 | Boyd et al. |
| 5,084,041 | A | 1/1992 | Oxley et al. |
| 5,229,327 | A | 7/1993 | Farnworth |
| 5,304,487 | A | 4/1994 | Wilding et al. |
| 5,333,675 | A | 8/1994 | Mullis et al. |
| 5,423,792 | A | 6/1995 | Oxley |
| 5,455,175 | A | 10/1995 | Wittwer et al. |
| 5,475,610 | A | 12/1995 | Atwood et al. |
| 5,508,197 | A | 4/1996 | Hansen et al. |
| 5,540,892 | A | 7/1996 | Kidd et al. |
| 5,576,218 | A | 11/1996 | Zurek et al. |
| 5,656,493 | A | 8/1997 | Mullis et al. |
| 5,674,742 | A | 10/1997 | Northrup et al. |
| 5,681,741 | A | 10/1997 | Atwood et al. |
| 5,795,547 | A | 8/1998 | Moser et al. |
| 5,832,543 | A | 11/1998 | Bosserman |
| 5,856,174 | A | 1/1999 | Lipshutz et al. |
| 5,928,880 | A | 7/1999 | Wilding |
| 5,935,858 | A | 8/1999 | Herst |
| 5,958,349 | A | 9/1999 | Petersen et al. |
| 5,972,716 | A | 10/1999 | Ragusa et al. |
| 6,210,382 | B1 | 4/2001 | Hogg |
| 6,210,958 | B1 | 4/2001 | Brust et al. |
| 6,374,684 | B1 | 4/2002 | Dority |
| 6,472,186 | B1 | 10/2002 | Quintanar et al. |
| 6,556,940 | B1 | 4/2003 | Tretiakov et al. |
| 6,645,191 | B1 | 11/2003 | Knerr et al. |
| 6,657,169 | B2 | 12/2003 | Brown et al. |
| 6,734,401 | B2 | 5/2004 | Bedingham et al. |
| 6,780,617 | B2 | 8/2004 | Chen |
| 6,783,736 | B1 | 8/2004 | Taylor et al. |
| 6,818,185 | B1 | 11/2004 | Petersen et al. |
| 6,875,602 | B2 | 4/2005 | Gutierrez |
| 6,881,541 | B2 | 4/2005 | Petersen et al. |
| 6,887,693 | B2 | 5/2005 | McMillan et al. |
| 6,889,468 | B2 | 5/2005 | Bedingham et al. |

(Continued)

FOREIGN PATENT DOCUMENTS

| | | | |
|---|---|---|---|
| DE | 4 022 792 A1 | 2/1992 | |
| DE | EP1000661 A1 * | 5/2000 | ................ B01L 3/00 |

(Continued)

OTHER PUBLICATIONS

European Office Action dated Nov. 6, 2012; Application No. 09713496.9-2113.

International Search Report and Written Opinion, for Corresponding PCT Application No. US2009/34446 A1 filed Feb. 19, 2009.

Northrup et al., A Miniature Integrated Nucleic Acid Analysis System, Automaition Technologies for Genome characterization, 1997, 189-204.

Boshoff-Mostert et al., Crack propagation in catalytic pellets due to thermal stresses. AICHE J. Aug. 1996, 2288-2294, 42.

Chaisson et al. , Tuberculosis in Africa—Combating an HIV driven crisis. N. Engl. J. Med., Mar. 13, 2008, 1089-1092, 358(11).

(Continued)

*Primary Examiner* — Stephanie K Mummert

(74) *Attorney, Agent, or Firm* — The Dobrusin Law Firm, PC

(57) ABSTRACT

A thermocycler apparatus and method for rapidly performing the PCR process employs at least two thermoelectric modules which are in substantial spatial opposition with an interior space present between opposing modules. One or multiple sample vessels are placed in between the modules such that the vessels are subjected to temperature cycling by the modules. The sample vessels have a minimal internal dimension that is substantially perpendicular to the modules that facilitates rapid temperature cycling. In embodiments of the invention the sample vessels may be deformable between: a) a shape having a wide mouth to facilitate filling and removing of sample fluids from the vessel, and b) a shape which is thinner for conforming to the sample cavity or interior space between the thermoelectric modules of the thermocycler for more rapid heat transfer.

24 Claims, 15 Drawing Sheets

(56) References Cited

U.S. PATENT DOCUMENTS

| | | | |
|---|---|---|---|
| 6,964,862 B2 | 11/2005 | Chen | |
| 6,987,253 B2 | 1/2006 | Bedingham et al. | |
| 7,138,254 B2 | 11/2006 | Jovanovich et al. | |
| 7,164,077 B2 | 1/2007 | Venkatasubramanian et al. | |
| 7,164,107 B2 | 1/2007 | Bedingham et al. | |
| 7,422,905 B2 | 9/2008 | Clague et al. | |
| 7,435,933 B2 | 10/2008 | Bedingham et al. | |
| 7,439,069 B2 | 10/2008 | Nippoldt et al. | |
| 7,482,116 B2 | 1/2009 | Birnboim | |
| 7,490,976 B2 | 2/2009 | Bucher | |
| 7,648,095 B2 | 1/2010 | Jagle | |
| 2006/0101830 A1 | 5/2006 | Cohen et al. | |
| 2006/0160243 A1 | 7/2006 | Tang et al. | |
| 2007/0111206 A1 | 5/2007 | Tyagi et al. | |
| 2007/0140919 A1 | 6/2007 | Clarkson et al. | |
| 2008/0003649 A1* | 1/2008 | Maltezos et al. | 435/91.2 |
| 2008/0193912 A1 | 8/2008 | Fong et al. | |
| 2008/0219889 A1 | 9/2008 | Schaefer et al. | |
| 2009/0011417 A1 | 1/2009 | Maltezos et al. | |
| 2009/0061450 A1 | 3/2009 | Hunter | |
| 2009/0162866 A1 | 6/2009 | Birnboim et al. | |
| 2010/0288059 A1 | 11/2010 | Viljoen et al. | |
| 2010/0291536 A1 | 11/2010 | Viljoen et al. | |

FOREIGN PATENT DOCUMENTS

| | | |
|---|---|---|
| EP | 0 350 675 A2 | 1/1990 |
| EP | 1000661 A1 | 5/2000 |
| WO | 98/43740 A2 | 10/1998 |
| WO | 1/15680 A1 | 3/2001 |
| WO | 2004/052527 A1 | 6/2004 |
| WO | 2005/113741 A1 | 12/2005 |

OTHER PUBLICATIONS

Davies et al., The diagnosis and misdiagnosis of tuberculosis, Int. J. Tuberc. Lung. Dis., Nov. 2008, 1226-1234, 12(11).

Davis et al.. The rheological properties of sputum, Biorheology, Apr. 1969, 11-21, 6(1).

Dziadek et al., Specificity of insertion sequence-based PCR assays for *Mycobacterium tuberculosis* complex, Int. J. Tuberc. Lung. Dis., Jan. 2001. 569-574, 5(6).

El-Haji et al., Detection of rifampin resistance in *Mycobacterioum tuberculosis* in a single tube with molecular beacons, J. Clin. Microbiol., Nov. 2001, 4131-4137, 39(11).

Flores et al., In-house nucleic acid amplification tests for the detection of *Mycobacterium tuberculosis* in sputum specimens: meta-analysis and meta-regression, BMC Microbiol., Oct. 2005, 55, 5.

Friedman et al., Capillary Tube Resistive Thermal Cycling, Anal. Chem., Jul. 15, 1998, 2997-3002, 70(14).

Global Health Diagnostics Forum, The right tools can save lives, Nature, Dec. 7, 2006, 681, 444.

Greco et al., Current evidence on diagnostic accuracy of commercially based nucleic acid amplification tests for the diagnosis of pulmonary tuberculosis, Thorax. Sep. 2006, 783-790, 61(9).

Griep et al., Kinetics of the DNA polymerase *Pyrococcus kodakaraensis*. Chemical Engineering Science, 2006, 3885-3892, 61.

Keeler et al., Reducing the global burden of tuberculosis: The contribution of improved diagnostics, Nature, Nov. 23, 2007, 49-57, 444 Suppl. 1.

Marras et al., Genotyping SNPs with molecular beacons, Methods Mol. Biol. 2003, 111-128, 212.

McEvoy et al., The role of IS6110 in the evolution of *Mycobacterium tuberculosis*, Tuberculosis (Edinb)., Sep. 2007, 393-404, 87(5).

Menzies et al., Risk of tuberculosis infection and disease associated with work in health care settings, Int. J. Tuberc. Lung Dis., Jun. 2007, 593-605, 11(6).

Menzies et, al., Tuberculosis among health care workes, N. Engl. J. Med., Jan. 12, 1995, 92-98, 332(2).

Musser, Antimicrobial agent resistance in mycobacteria: genetic insights, Clin. Microbiol, Rev., Oct. 1995, 496-514, 8(4).

Muthupillai et al., Magnetic resonance elastography by direct visualization of propagating acoustic strain waves, Science, Sep. 29, 1995, 1854-1857, 269.

Negi et al., Diagnostic potential of IS6110, 38kDa, 65kDa and 85B sequence-based polymerase chain reaction in the diagnosis of *Mycobacterium tuberculosis* in clinical samples, Indian. J. Med. Microbiol. Jan. 2007, 43-49, 25(1).

Nelson et al., Elastic contributions dominate the viscoelastic properties of sputum from cystic fibrosis patient, Biophys. Chem., Dec. 20, 2004, 193-200, 112.

Othman et al., Microscopic magnetic resonance elastography (muMRE), Magnetic Resonance in Medicine, Sep. 2005, 605-615, 54.

Perkins et al., Progress towards improved tuberculosis diagnostics for developing countries, Lancet, Mar. 18 2006, 942-943, 367.

Ramaswamy at al., Molecular genetic basis of antimicrobial agent resistance in *Mycobacterium tuberculosis*: 1998 update, Tauber. Lung Dis., 1998, 3-29, 79.

Riska et al., Molecular determinants of drug resistance in tuberculosis, Int. J. Tuberc. Lung Dis., Feb. 2000, S4-10, 4(2 Suppl 1).

Sarmiento et al., Assessment by meta-analysis of PCR for diagnosis of smear-negative pulmonary tuberculosis, J. Clin. Mierobiol,, Jul. 2003, 3233-3240, 41(7).

Shah et al., Extensively Drug-Resistant Tuberculosis in they United States 1993-2007, JAMA, Nov. 7, 2008, 2153-2160, 300(1).

Singh et at, Comparative evaluation of FASTPlaque assay with PCR and other conventional in vitro diagnostic methods for the early detection of pulmonary tuberculosis, J. Clin. Lab. Anal., 2008, 367, 22(5).

Somoskovi et al., The molecular basis of resistance to isoniazid, rifampin, and pyrazinamide in *Mycobacterium tuberculosis*, Respir. Res., 2001, 164-168, 2(3).

Storla et al., A systematic review of delay in the diagnosis and treatment of tuberculosis, BMC Public Health, Jan. 14, 2008, 15, 8.

Sun et al., Comparison of gyrA gene mutations between laboratory-selected ofloxacin-resistant *Mycobacterium tuberculosis* strains and clinical isolates, Int. J. Antimicrob, Agents., Feb. 2008, 115-112, 31(2).

Telenti, Genetics and pulmonary medicine. 5. Genetics of drug resistant tuberculosis, Thorax, Sep, 2008, 793-797, 53.

Thierry et al., Characterization of a *Mycobacterium tuberculosis* insertion sequence, IS6110, and its application in diagnosis, J. Clin. Microbiol., Dec. 1990, 2668-2673, 28(12).

Valente et al., A kinetic study of in vitro lysis of *Mycobacterium smegmatis*, Chemical Engineering Science, 2009, 1944-1952, 64.

Van Soolingen et al., Comparison of various repetitive DNA elements as genetic markers for strain differentiation and epidemiology of *Mycobaderium tuberculosis*, J. Clin. Microbiol., Aug. 1993, 1987-1995, 31.

Viljoen et al., A macroscopic kinetic model for DNA polymerase elongation and the high-fidelity nucleotide selection, Computational Biology and Chemistry, Apr. 2005, 101-110, 29.

Wang et al., Fluoroquinolone resistance in *Mycobacterium tuberculosis* isolates; associated genetic mutations and relationship to antimicrobial exposure, J. Antimicrob. Chemother., May 2007, 860-865.

Wittwer et al., Minimizing the Time Required for DNA Amplification by Efficient Heat Transfer to Small Samples, Anal. Biochem., May 1, 1990, 328-331, 186(2).

World Heat Organization, Global tuberculosis control—epidemiology, strategy, financing, WHO Report 2009, WHO/HTM/TB/2009. 411.

European Communication dated Nov. 4, 2014; Appln. No. 09713496. 9.

Canadian Office Action dated Feb. 24, 2015; Application No. 2,716,337.

* cited by examiner

THERMOCYCLER AND SAMPLE VESSEL FOR RAPID AMPLIFICATION OF DNA

CLAIM OF BENEFIT OF FILING DATE

The present application claims the benefit of the filing date of PCT Application Serial No. PCT/US2009/034446 (filed Feb. 19, 2009) (Published as WO 2009/105499) and U.S. Provisional Application Ser. No. 61/066,365 (filed Feb. 20, 2008), the contents of which are hereby incorporated by reference in their entirety.

FIELD OF THE INVENTION

The present invention generally relates to apparatus and methods for rapid thermocycling for the automated performance of the polymerase chain reaction (PCR), and more particularly, to methods, thermocyclers, and sample vessels for automatically conducting rapid deoxyribonucleic acid (DNA) amplification using PCR.

BACKGROUND OF THE INVENTION

Thermocyclers and sample vessels are employed for the automated performance of the polymerase chain reaction (PCR). The process of deoxyribonucleic acid (DNA) amplification with PCR has become one of the most utilized techniques in molecular biology and conducting thermal cycling protocols is paramount to the technique. Various automated instruments to perform PCR thermocycling have been described in literature and are commercially available from numerous manufacturers.

PCR thermocycling instruments can generally be represented by three major classifications:

1) Conventional heat block cyclers which employ one or more heating/cooling apparatuses in contact with a thermally conductive block wherein PCR sample vessels are contained,
2) Capillary thermocyclers in which samples are contained within cylindrical glass or plastic capillaries which are exposed to convective heat transfer on their exterior, and
3) Microfabricated thermocyclers in which PCR samples are contained within etched, milled, or molded micrometer-scale structures and thermal cycling is achieved by different heat transfer methods such as resistive heating.

All PCR thermocyclers seek to perform the temperature cycling necessary to facilitate the repeated PCR steps of denaturation, annealing, and elongation each of which generally occurs at different temperatures. As such, thermocycler performance is primarily based upon the thermocycler heating and cooling rates to reach these desired temperatures and by the hold time required for the heat to conduct to/from the PCR sample edge to the sample center. A high-performance thermocycler will rapidly change temperatures due to optimal thermocycler design and the high-performance thermocycler will have minimal denaturation, annealing, and elongation hold times due to optimal sample vessel design. The combined effect of temperature ramp rates and temperature hold times is what is critical to the performance of the instrument.

Exemplary instruments and apparatus employed for the performance of PCR thermocycling are disclosed in U.S. Pat. No. 6,556,940 to Tretiakov et al, U.S. Pat. No. 5,455,175 to Wittwer et al, U.S. Pat. No. 6,472,186 to Quintanar et al, U.S. Pat. No. 5,674,742 to Northrup et al, U.S. Pat. No. 5,475,610 to Atwood et al, U.S. Pat. No. 5,508,197 to Hansen et al, U.S. Pat. No. 4,683,202 to Mullis, U.S. Pat. No. 5,576,218 to Zurek et al, U.S. Pat. No. 5,333,675 to Mullis et al, U.S. Pat. No. 5,656,493 to Mullis et al, U.S. Pat. No. 5,681,741 to Atwood et al, U.S. Pat. No. 5,795,547 to Moser et al, U.S. Pat. No. 7,164,077 to Venkatasubramanian et al, U.S. Pat. No. 6,657,169 to Brown et al, U.S. Pat. No. 5,958,349 to Petersen et al, U.S. Pat. No. 4,902,624 to Columbus et al, U.S. Pat. No. 5,674,742 to Northrup et al, U.S. Pat. Nos. 6,734,401, 6,889,468, 6,987,253, 7,164,107, and 7,435,933 each to Bedingham et al, WO 98/43740, DE 4022792, WO/2005/113741, Northrup, M. Allen, et al, "A Miniature Integrated Nucleic Acid Analysis System", Automation Technologies for Genome characterization, 1997, pp. 189-204, Wittwer, Carl T., et al, "Minimizing the Time Required for DNA Amplification by Efficient Heat Transfer to Small Samples", Anal. Chem. 1998, 70, 2997-3002, and Friedman, Neal A., et al, Capillary Tube Resistive Thermal Cycling", The 7$^{th}$ International Conference on Solid-State Sensors and Actuators, 924-926.

While each instrument design has its own benefits, all are subject to certain disadvantages. Heat block thermocyclers can generally handle a large number of samples with volumes of approximately 20-200 μl each. The conically shaped sample vessels used in most block cyclers are particularly advantageous for loading and unloading the sample mixtures by manual or automated pipettors. By using thermoelectric modules (Peltier devices) to provide heat pumping to the block, these thermocyclers require only electrical power to operate. However, these devices suffer from slow ramp rates and long minimum temperature hold times; usually requiring 1-3 hours to complete standard 30-cycle PCR protocols. The slow speed of these devices is generally attributable to the large thermal mass of the heat block, the use of thermoelectric modules on only one side of the heat block, the large wall thickness and poor thermal conductivity of the sample vessel, and the internal thermal resistance of the sample mixture itself.

To overcome slow ramp rates, some designs employ glass capillaries, such as disclosed in U.S. Pat. No. 5,455,175 to Wittwer et al, U.S. Pat. No. 6,472,186 to Quintanar et al, WO/2005/113741, and Friedman et al Capillary Tube Resistive Thermal Cycling", The 7$^{th}$ International Conference on Solid-State Sensors and Actuators, 924-926. The glass capillaries provide a higher surface area to volume ratio and greater thermal conductivity than the conical sample vessels used in heat block thermocyclers, thereby creating the capability for rapid thermocycling. Hot-air thermocyclers using glass capillaries as disclosed in U.S. Pat. No. 5,455,175 to Wittwer et al, eliminate the thermal mass of heat blocks, but have relatively poor convection heat transfer properties. Improving on this idea, PCR using pressurized gas has been accomplished in a matter of minutes as disclosed in U.S. Pat. No. 6,472,186 to Quintanar et al and WO/2005/113741. However, as most molecular biology labs do not have readily available high pressure air, the application of pressurized gas devices is inconvenient and limited for many users. Also, glass capillaries are known to be fragile, more expensive, and require additional steps to load and unload the sample mixtures.

Microfabricated thermocyclers, as disclosed for example in U.S. Pat. No. 5,674,742 to Northrup et al, incorporate similar high surface area to volume ratios through the use of etched structures, usually in glass or silicon. While capable of fast thermocycling and integration with other laboratory techniques by the use of microfluidics, the manufacturing cost associated with these thermocyclers is high. As with glass capillaries, loss of enzyme activity and absorption of DNA onto the vessel surface are also problematic; and a carrier protein (e.g. bovine serum albumin) is recommended to reduce these undesired aspects. Additionally, these thermocyclers are usually limited to small reaction volumes on the order of a few microliters or less which is too small of a volume for many medically relevant PCR techniques.

Several advances have been made in the performance of block thermocyclers over the past decade. These are generally attributed to the use of thin-walled sample vessels with low thermal resistance as disclosed in U.S. Pat. No. 5,475,610 to Atwood et al, and low thermal mass sample blocks as disclosed in U.S. Pat. No. 6,556,940 to Tretiakov et al. Despite these advances, PCR cycling times and maximum reaction volumes for normal temperature protocols are far from optimal. In the apparatus of U.S. Pat. No. 6,556,940 Tretiakov et al, a rapid heat block thermocycler has a similar arrangement of components to conventional heat block cyclers. However, the Tretiakov et al instrument achieves fast thermocycling through the use of: 1) a low profile, low thermal mass, and low thermal capacity heat block, 2) at least one thermoelectric module, and 3) ultra-thin wall sample wells. This thermocycler can achieve much faster ramp rates than typical heat block cyclers; with PCR being capable of being performed in 10-30 minutes. Unfortunately, the reaction volumes are limited to 1-20 μL. Tretiakov et al has addressed two of the major handicaps of traditional heat block cyclers by reducing the thermal mass of the heat block and reducing the thermal resistance (i.e. wall thickness) of the sample vessel. However, the internal thermal resistance of the sample itself still limits the speed of the instrument. With the use of a conical shaped well, increases in reaction volumes changes the surface area to volume ratio and thus the internal thermal resistance becomes of greater significance. Therefore, larger volumes in the Tretiakov et al instrument would require longer hold times (and thereby increase run time) to enable the internal regions of the sample to reach proper temperatures needed for efficient PCR. The reaction volume is thus limited by Tretiakov et al to 20 μL for rapid PCR protocols. Additionally, larger volumes imply an increase in block height which leads to a larger heat block and thermal mass. Alternatively, a large vessel radius would increase internal thermal resistance.

U.S. Pat. No. 5,958,349 to Petersen et al discloses a sample vessel and thermocycler with abbreviated cycle times when compared to traditional block cyclers. The instrument takes advantage of a sample vessel with two major opposing faces through which the heat transfer primarily occurs. The sample vessel has a plurality of minor faces which join the major faces, a sample port, and a triangular shaped bottom that is optically advantageous. Sample heating is achieved through the use of heating elements in contact with the major faces; cooling is done by a chamber surrounding both the vessel and heating elements. The Petersen et al reaction vessel has a thermal conductance ratio of major to minor faces of at least 2:1. Petersen et al may employ different materials for the faces or different thicknesses, with the major faces having a higher conductance that allows for geometry modification of the vessel while still maintaining the thermal conductance ratio. This allows for the surface area ratio of major to minor faces to be less than 2:1, and subsequently condones a relatively large through thickness dimension (perpendicular to the heat transfer apparati). A high discrepancy (i.e. 10:1) of thermal conductances of the major to minor faces is allowed. A characteristic time is needed to transfer heat from the sample exterior to the interior regions to facilitate efficient PCR throughout the entire reaction mixture. By specifying a thermal conductance ratio and allowing large internal distances, the sample mixture itself can be rate-limiting. The internal thermal resistance of the sample mixture and its effect on the thermal kinetics of the system are overlooked by Petersen et al. In contrast, the sample vessel thermal path length was considered in U.S. Pat. No. 4,902,624 to Columbus et al. However, the design complexity of the sample vessel channels and reaction chamber proposed by Columbus et al are detrimental to heat transfer and are relatively costly to implement.

Many thermocyclers, especially heat block cyclers, use thermoelectric modules (Peltier devices) to facilitate temperature cycling. The sample vessel geometry dictates that a heat block which is complementary to the conical sample vessels be present between the thermoelectric module and the sample vessel. This heat block adds thermal mass to the system and slows cycling performance. Some in the art, such as U.S. Pat. No. 6,556,940 to Tretiakov et al, and U.S. Pat. Nos. 6,734,401, 6,889,468, 6,987,253, 7,164,107, and 7,435,933 each to Bedingham et al disclose the use of at least one thermoelectric module. Generally, multiple thermoelectric module configurations are 1) in stackable configurations to achieve higher temperature differences between the outside faces or 2) to create temperature differences among sample vessels as with temperature gradient cyclers. Multiple modules may also be used in multiple heat block cyclers that can run separate thermocycler protocols simultaneously. However, the multiple modules are used only on one side of the heat block (generally the bottom side).

Conventional heat block instruments would not substantially benefit from the presence of a thermoelectric module on the top surface of the heat block. A top thermoelectric module cannot practically be employed in conventional block cyclers as is especially evident in most commercially available block cyclers in which heated lids are utilized to reduce detrimental sample evaporation/condensation. The heated lids do manipulate the temperature of a portion of the sample vessel but only in an isothermal manner and there is a significant insulating air gap present between the lid and the sample mixture making it unfeasible to conduct temperature cycling at this lid surface. Therefore, the heated lid serves a limited function and does not directly participate in the temperature cycling protocol to achieve PCR.

The thermocycler apparatus of the present invention has a unique arrangement of thermocycler components and sample vessels that enable rapid temperature cycling. The use of two or more thermoelectric devices placed in spatial opposition to one another yields very dense heat pumping to samples within the interior space. In embodiments of the present invention, thirty cycles of PCR can be completed in mere minutes, significantly less than any other solid-state apparatus and on par with the fastest of compressed air thermocyclers.

Another aspect of the present invention that enables rapid PCR is the use of specifically designed sample vessels. Not all sample vessels are capable of rapid temperature cycling even with thin walls. Efficient PCR demands that all regions of the sample reach the desired set point temperatures at each PCR step. Thus, outer regions of the reaction mixture must be held at the desired temperature whilst the interior regions reach the desired temperature. For example, conical tubes used in standard heat block cyclers recommend hold times of about 30 seconds even though PCR steps (such as denaturation and annealing) are nearly instantaneous events. Despite their advantages for sample loading and larger volumes, standard conical PCR tubes are not amenable to rapid PCR. The samples vessels disclosed in the present invention are marked by several key characteristics. The sample vessels employed in the present invention are easy to load similar to standard conical PCR tubes when outside of the thermocycler, yet can be used for rapid PCR by limiting the thickness dimension critical to temperature cycling when inserted into the thermocycler. Most importantly, larger reaction volumes can be processed without any substantial increase in PCR runtimes, a consequence of the novel design of the invention. In comparison to the vessel of U.S. Pat. No. 5,958,349 to Petersen et al., the sample vessel of the present invention need not have a plurality of minor faces. The sample vessel of the present invention may include cylindrical regions that are continuous. Instead of defined edges as in Petersen et al., the continuity and deformability of the sample vessels of the present invention facilitates improved thermal contact. Also, rapid PCR is not reliant on specifying a thermal conductance ratio, but rather the heat transfer kinetics from outer sample regions closer to the heat source (or sink) to the inner regions. In contrast to the sample vessel of U.S. Pat. No. 4,902,624 to Columbus et al., the sample vessel of the present invention is much simpler in design and thus manufacture, while at the same time performing at much higher speeds. The deformable and accessible nature of sample vessels disclosed herein offer unique advantages for sample loading and thermal contact than non-deformable sample vessels such as glass capillary and conical sample vessels.

Fourier's law of conduction and the thermal conductance of the system (conductivity divided by the material thickness) have been referenced in the design of many PCR thermocyclers and sample vessels. While thermal conductance is a relevant design parameter for steady state heat transfer, the temperature cycling of PCR is a dynamic process. As such, it is more apt to include the time dependency through the application of the heat diffusion equation, a parabolic partial differential equation that is derived from Fourier's law of conduction and the conservation of energy:

$$\frac{\partial T}{\partial t} = \kappa \nabla^2 T \text{ where } \kappa = \frac{k}{\rho * C_p}$$

The change in temperature (T) over time (t) depends upon the thermal diffusivity (κ) and the Laplacian of the temperature ($\nabla^2 T$). Thermal diffusivity includes the thermal conductivity (k) and the thermal mass ($\rho * C_p$) where p is the material density and $C_p$ is the heat capacity. The Laplace operator is taken in spatial variables of the physical system. The unassuming heat equation is quite powerful when applied to PCR thermocycling and its solution can be found for different physical systems by a variety of analytical or numerical methods. Qualitatively, one can extract the key design parameters directly from the above equation. To maximize speed, the thermal conductivity should be large while the thermal mass small. A small thermal mass is achieved by keeping the spatial dimension to a minimum.

In embodiments of the invention, the heat diffusion equation is applied to all regions, yielding a system of coupled equations. The temperature behavior should be elucidated not only for regions on the exterior of the vessel and the vessel wall, but also for the sample mixture itself. During PCR temperature cycling, overshoot of the denaturation temperature is undesirable because of thermal damage to the DNA and loss of enzyme activity. An undershoot of the annealing temperature is harmful to PCR because of possible misannealing events. Therefore, a characteristic time is employed to allow for proper temperatures to occur throughout the sample while not allowing significant overshoots or undershoots at the sample mixture exterior. Since the thermal diffusivity and mass of the sample mixture and temperature set points are dictated by the PCR process, limiting one of the spatial dimensions of the sample mixture is the best method to facilitate rapid temperature cycling. By application of these fundamental principles of heat transfer, the present invention provides a geometry and arrangement of components and sample vessel design for rapid PCR thermocycling. By limiting the internal distance of the sample mixture and placing thermoelectric modules in intimate proximity to the sample vessel, the present invention achieves rapid sample thermocycling and efficient PCR. Additionally, the arrangement of thermoelectric modules according to the present invention not only reduces the distance from the heat transfer sources to the reaction mixture, it increases the effective heat pumping density available to the samples.

SUMMARY OF THE INVENTION

The present invention provides a process and apparatus for rapid thermocycling of biological samples to perform a polymerase chain reaction for amplification of DNA. A PCR reaction mixture is contained within a sample container or vessel having a small dimension critical to heat transfer from the external regions to the internal regions of the mixture. At least two thermoelectric modules are placed in substantial spatial opposition in which any number of sample vessels are placed in the interior region between the thermoelectric modules. When current is applied to the thermoelectric modules, the samples are thereby heated or cooled (dependent on current direction) to the desired temperatures to perform PCR from two opposing directions driven by the opposing thermoelectric modules. At least one temperature measurement device is present to provide information so that the temperature can be automatically controlled by the apparatus through any desired temperature cycling PCR protocol.

The present invention also provides a number of reaction vessels for containing a biological sample to enable the performance of rapid thermocycling. The vessels have a small dimension when placed within the thermocycling apparatus. This critical dimension is substantially normal to the heat source (or sink) face, such that the internal thermal resistance of the biological sample is kept minimal. In preferred embodiments, the reaction vessels may be substantially deformable, such that the user may easily load and unload the biological sample in the native vessel state through a relatively large opening. Yet, the reaction vessel will assume a substantially different shape when inserted into the thermocycler for the execution of rapid PCR, such as a shape which conforms to the sample cavity between the opposing thermoelectric modules so as to increase the surface area for heat transfer between the sample and the thermoelectric modules or heat sinks. The reaction vessels may be thin-walled, optically clear, and made out of a material capable of withstanding the temperatures experienced in PCR, such as but not limited to polypropylene. In other embodiments glass capillaries may be employed within the apparatus.

BRIEF DESCRIPTION OF THE DRAWINGS

The present invention is described in the detailed description which follows, in reference to the noted plurality of drawings by way of non-limiting examples of exemplary embodiments of the present invention.

DETAILED DESCRIPTION OF THE INVENTION

Figure 1:
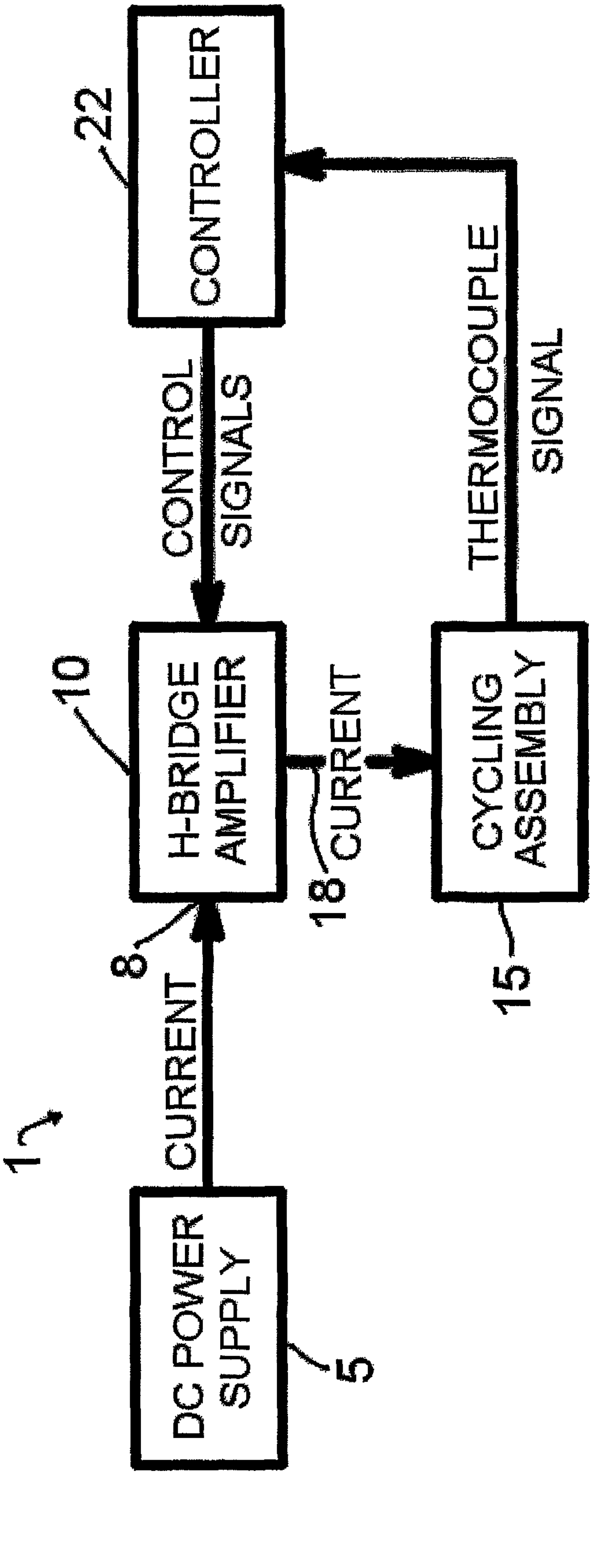
FIG. 1 schematically shows the thermocycler components of the present invention.

The present invention provides a process for rapid thermocycling of biological samples. In embodiments of the present invention, two or more solid state thermoelectric devices are placed in substantial opposition with an interior region that can accept any number of sample vessels. The thermoelectric devices are spatially oriented to one another such that the interior region is heated or cooled simultaneously by both devices when directional current is applied to the devices. The present invention provides a process for rapid thermocycling of the biological samples to perform the polymerase chain reaction (PCR) using the thermoelectric devices. The apparatus of the present invention achieves PCR amplification using thermoelectric devices placed in substantial opposition to one another. The present invention also provides a vessel for containing biological samples that enable rapid thermal cycling by its limited dimensions. The sample vessels for containing biological samples can hold large PCR reaction volumes of about 50 μL to about 250 μL, which may be processed without a substantial increase in thermocycling times. The apparatus for rapid thermocycling permits the processing of variable reaction volumes without significant changes to thermocycling times. Specifically, both large reaction volumes and small reaction volumes can be processed rapidly. The rapid thermocycling may be achieved for one or more biological samples. In embodiments of the invention, the reaction vessel may have one internal dimension (the distance from the insides opposing surfaces of the vessel walls) that is from about 0.4 mm to about 2.5 mm, for example no greater than about 2.0 mm, when placed within a thermocycler unit and measured substantially perpendicular to the opposing faces of the thermoelectric modules.

The apparatus of the present invention decreases the thermal cycling time needed for DNA amplification over other Peltier-based systems. In embodiments of the present invention, 30 standard cycles of PCR can be completed in approximately 5 minutes, whereas known, conventional Peltier-based thermocyclers require about 10 minutes minimum. Another advantage of the present invention is that larger reaction volumes of about 50 μL to about 250 μL can also be processed under rapid thermal cycling conditions, whereas other Peltier-based and pressurized gas instruments are limited to about 3-25 μL as in the systems of U.S. Pat. No. 6,556,940 to Tretiakov et al, and U.S. Pat. No. 6,472,186 to Quintanar et al. The ability to process larger reaction volumes is highly attractive for many applications as a means to increase PCR sensitivity or dilution of inhibitors. In addition, the vessels provided in the present invention are ideally suited for rapid PCR because of the limited dimension critical for heat transfer when the vessels are placed within the thermocycler, yet the vessels are comparable in ease of loading/unloading and cost to standard PCR tubes. Fourth, the present invention is compatible with optical detection so that rapid amplification and detection may be carried out.

A representative diagram of the major components of the thermocycler apparatus 1 of the present invention for conducting rapid thermocycling on any number of biological samples is shown in FIG. 1. A direct current power supply 5 with appropriate specifications is electrically connected to the power input 8 of an H-bridge electronic circuit 10. The lead wires of the thermoelectric modules within the cycling assembly 15 are connected to the power output 18 of the H-bridge circuit 10. One or multiple temperature measurement devices, such as but not limited to thermocouples, are present in the assembly 15 and provide information to a controller 22, which in turn controls the behavior (for example, electrical power and directionality) of the H-bridge 10. In embodiments of the invention, the thermocouples may be located in a sample vessel, a sample vessel holder, a module laminate, or combinations thereof. The controller 22 is programmable by the user and may be operated via a multiplicity of computer-controlled operations. Various techniques well known in the art of control theory, such as PID control, can be utilized to subject the samples to PCR temperature protocols specified by the user. In embodiments of the invention where two or more pairs of thermoelectric modules are employed, the controller may control the pairs of thermoelectric modules so that the modules run independent temperature protocols simultaneously, or the same temperature protocols simultaneously.

The use of thermoelectric devices (Peltier effect) for heating and cooling applications is well known in the art. Conventional, commercially available thermoelectric devices or Peltier devices may be employed in the apparatus and methods of the present invention. These Peltier devices are generally comprised of electron-doped n-p semiconductor pairs that act as miniature heat pumps. When current is applied to the semiconductor pairs, a temperature difference is established whereas one side becomes hot and the other cold. If the current direction is reversed, the hot and cold faces will be reversed. Usually an electrically nonconductive material layer, such as aluminum nitride or polyimide, comprises the substrate faces of the thermoelectric modules so as to allow for proper isolation of the semiconductor element arrays. In a preferred embodiment of the present invention, the opposing thermoelectric modules are spatially oriented such that when positive current is applied, both interior faces become hot and heat the sample vessels. When the current direction is reversed via the H-bridge, both of the interior faces become cold, and the sample vessels are cooled. Alternatively, it is facile to see that the wiring of the modules or apparatus electronics could be modified to produce the same heating and cooling effects.

Figure 2:
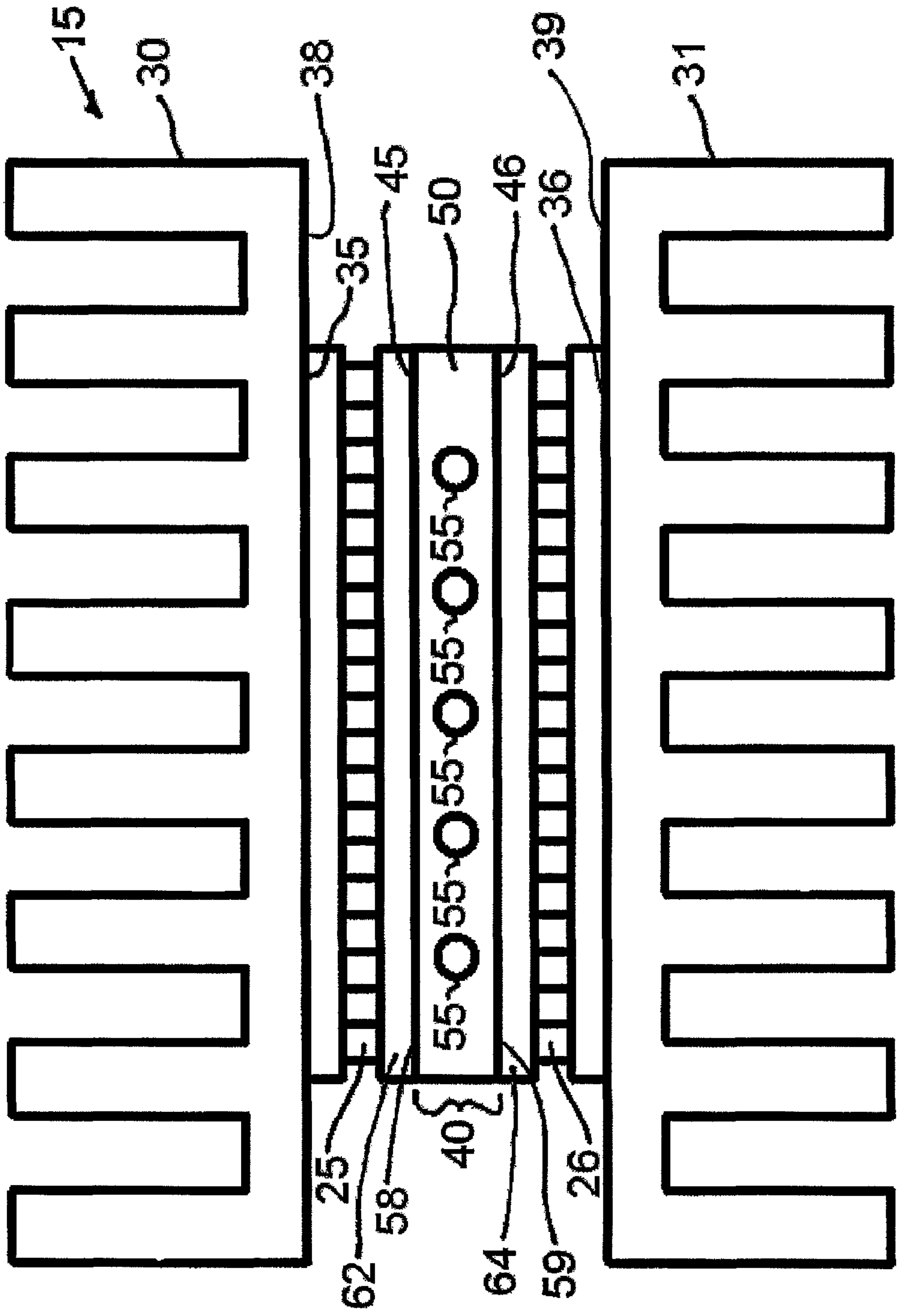
FIG. 2 is a top schematic view of an embodiment of the cycling assembly of the present invention for receiving capillaries.

An example of a cycling assembly 15 is shown in FIG. 2. The Peltier devices or thermoelectric modules 25 and 26 are placed in substantial spatial opposition to one another. In preferred embodiments the opposing thermoelectric modules are oriented at least substantially vertically with their major opposing heat transfer surfaces being vertically oriented and at least substantially parallel to each other. Heat sinks 30 and 31 may be placed in thermal contact with the exterior faces 35 and 36, respectively of the thermoelectric modules 25 and 26, respectively to dissipate heat and allow for good heat pumping efficiency of the thermoelectric modules 25, 26. The heat sinks 30, 31 are designed as well known in the art of heat exchanger design, and are generally made of copper or aluminum. Generally, the heat sink inner surface 38, 39 will be larger than the mating outer face 35, 36 respectively of the thermoelectric module 25, 26, respectively. In the region 40 between the interior faces 45 and 46 of the thermoelectric modules 25, 26, respectively, a machined material or sample holder 50 is present such that sample vessels may be inserted into the open areas of the machined material 50. This material has a high thermal conductivity but low thermal mass, such as but not limited to aluminum or silver, to facilitate rapid heat transfer and temperature uniformity. To facilitate good contact among the heat sinks 30, 31, thermoelectric modules 25, 26, and machined interior metal 50, heat sink compound or thermal paste may be applied to mating surfaces. Additionally, one or more fans (not shown) may be present to aid in heat dissipation from the heat sinks through either unidirectional or impingement methods. The interior material 50, in FIG. 2 has one or more holes, passageways, or cavities 55 fabricated in it that are toleranced such that a close fit is obtained when capillaries are inserted. Similarly, the holes 55 could take on an oval shape to accommodate oval glass or plastic capillaries to allow for larger reaction volumes. The outer walls or outer surfaces 58, 59 of the interior material or sample holder 50 are in direct contact with the interior faces 45 and 46 of the thermoelectric modules 25, 26, respectively for efficient, rapid heat transfer between the sample holder 50 and samples contained therein 55 and the thermoelectric modules 25, 26. Alternatively, sample holder 50 and the inner opposing substrates 62, 64 of thermoelectric modules 25, 26, respectively could be made of one solid surface with high thermal conductivity but low electrical conductivity and low thermal mass, such as but not limited to bare or metallized ceramics.

Figure 3:
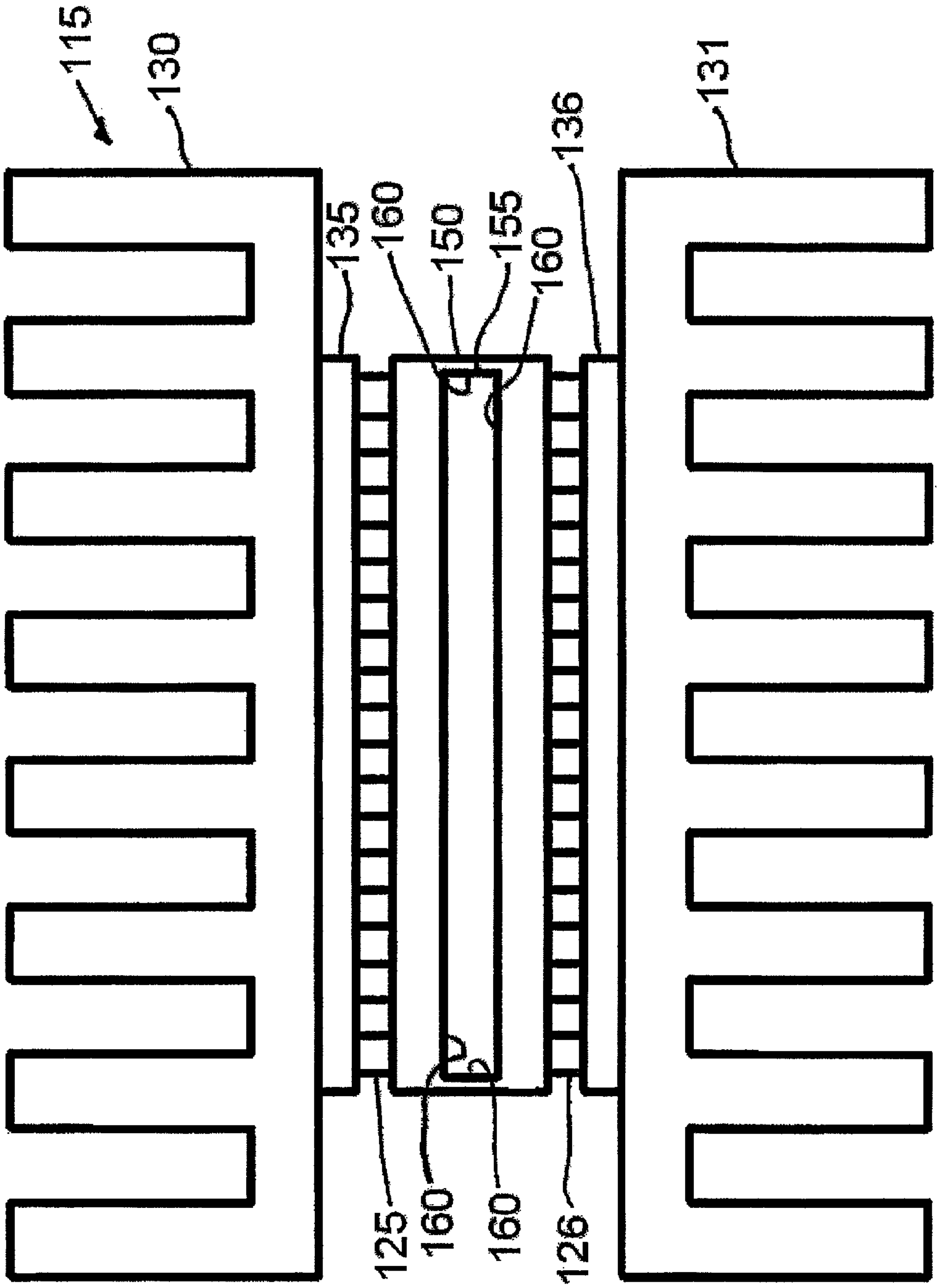
FIG. 3 is a top schematic view of an embodiment of the cycling assembly of the present invention with an open slot for receiving sample vessels.

As shown in FIG. 3, a slotted version of the cycling assembly 115 is another embodiment of the present invention. In this embodiment and applicable to other embodiments of the present invention, the thermoelectric modules 125 and 126 are placed in substantial spatial opposition to one another, but have heat sinks 130 and 131, respectively, integrated into the outer substrate 135, 136, respectively of the thermoelectric modules 125, 126, respectively. In other words, the outer substrates 135, 136 of the thermoelectric modules 125, 126 are fabricated into the form of heat sinks 130, 131 before bonding to the Peltier arrays 125, 126. Similarly, the inner substrate or sample vessel holder 150 is shared by both thermoelectric modules 125 and 126 upon fabrication. This results in a rather compact and integrated cycling assembly 115. In the interior cavity or slot 155 of the inner substrate 150, sample vessels are inserted such that a substantial portion of the vessel walls comes into good thermal contact or direct contact with the interior or cavity walls 160 of the slot 155 of thermoelectric modules 125, 126 to allow for rapid thermocycling. In embodiments of the invention, the inner substrate 150 may have a plurality of slots arranged along the central longitudinal axis of the inner substrate 150 for simultaneously accommodating a plurality of sample vessels.

Figure 4:
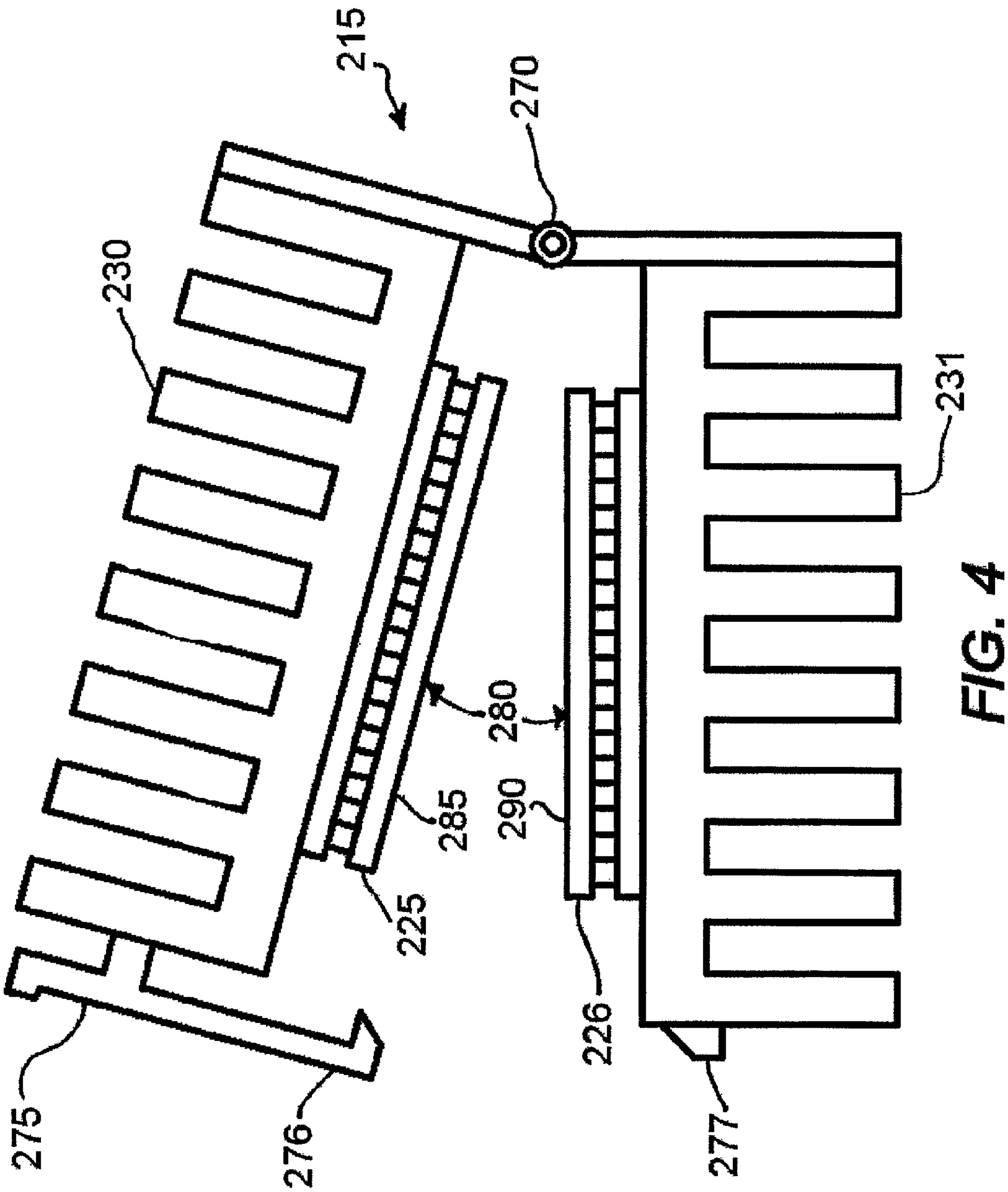
FIG. 4 is a top schematic view of an embodiment of the cycling assembly of the present invention for thin disk or thin film sample vessels

FIG. 4 illustrates a hinged embodiment of a cycling assembly 215 of the present invention. As in the previously described embodiments of FIGS. 2 and 3, the hinged cycling assembly 215 has thermoelectric modules 225 and 226 and heat sinks 230 and 231. In this embodiment, a hinge mechanism 270 and latch mechanism 275 may be utilized. The hinge 270 is hingedly attached to an end of the heat sinks 230 and 231 and enables opening of the interior space 280 between the thermoelectric modules 225 and 226 to allow for facile insertion of sample vessels into the interior space 280, especially substantially deformable or "thin-disk" vessels. The latch mechanism 275 includes a latch 276 attached to heat sink 230 and a ledge or protrusion 277 attached to heat sink 231. The protrusion 277 is engaged by latch 276 when the hinge 270 is closed to keep the heat sinks 230 and 231 in a fixed position. When the hinge 270 is closed and latch mechanism 275 engaged, substantial portions of the sample vessels come into good thermal contact or direct contact with the inner substrates 285, 290 of the thermoelectric modules 225 and 226, respectively, to enable rapid thermocycling. Alternatively, the hinge mechanism 270 could be detachable with one or more latch mechanism 275 and latch 276 to keep the heat sinks 230 and 231, and thermoelectric modules 225 and 226, in a fixed position when latched.

In embodiments of the invention, such as those of FIGS. 2, 3, and 4, the thermoelectric modules of each pair may be positioned with the module faces of each thermoelectric module pair in substantial opposition such that the semiconductor elements in the opposing modules are separated by a distance of from about 0.5 mm to about 10.0 mm. In such embodiments, a sample vessel can be utilized wherein the distance between the inner surfaces of the sample vessel critical to heat transfer, or the distance between opposing inner surfaces of the sample vessel in a direction substantially perpendicular to the surfaces of the module faces is no less than about 0.5 mm and no more than about 2.5 mm.

In embodiments of the invention, the thermocycler apparatus of the present invention may include more than one cycling assembly. This is an attractive feature because two or more PCR protocols can be run simultaneously, or two or more cycling assemblies can be run under an identical protocol. For a multiple protocol apparatus, one additional H-bridge amplifier and one additional temperature measurement device may be included for each additional cycling assembly. The additional set or additional sets of thermoelectric modules may be connected to a unique H-bridge amplifier while an additional temperature measurement device or set of temperature measurement devices sends information to the controller. In another embodiment of the multiple protocol apparatus, heat sinks may be commonly shared among the cycling assemblies.

Figure 5A:
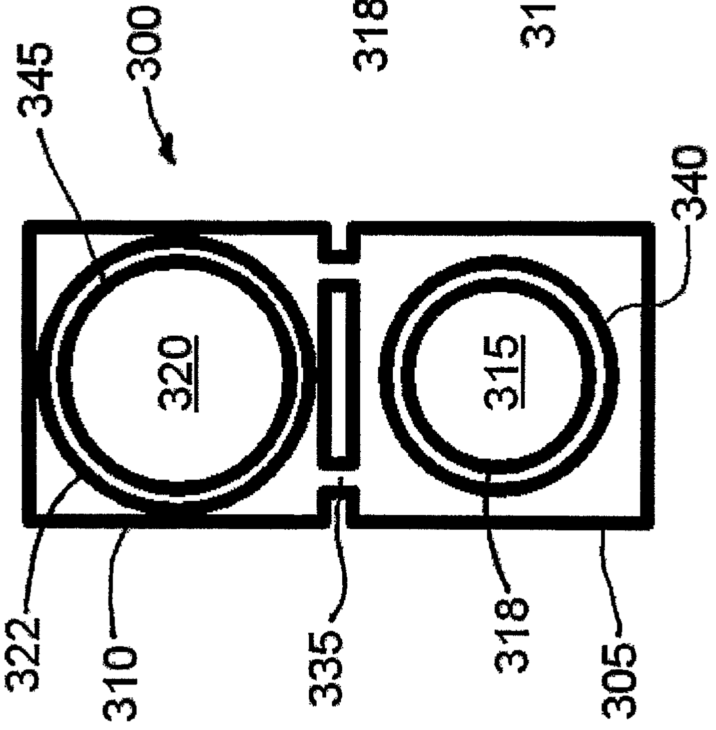
FIG. 5A is a top view of a thin disk embodiment of the sample vessel of the present invention.
Figure 5B:
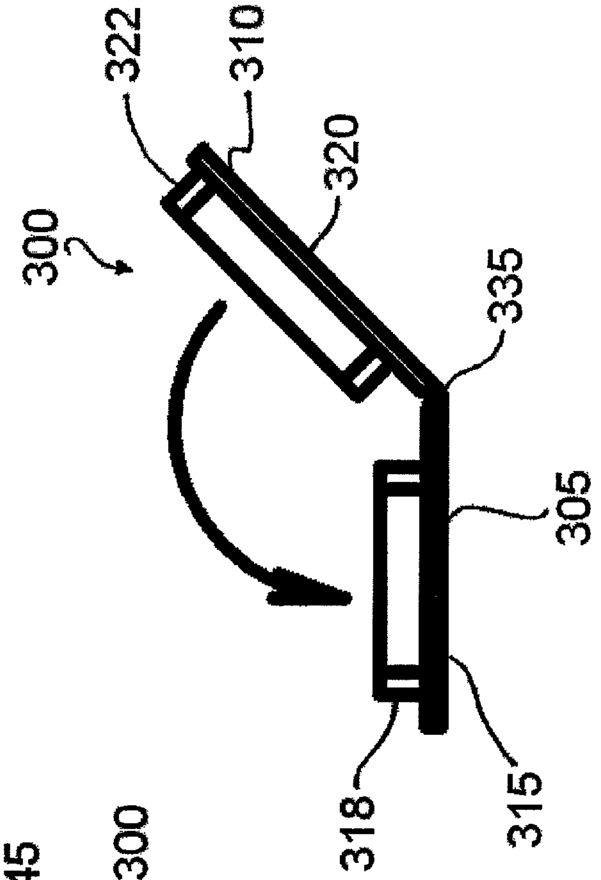
FIG. 5B is a side view of a thin disk embodiment of the sample vessel of FIG. 5A in the process of being closed.

Another aspect of the present invention concerns reaction or sample vessels for conducting rapid PCR. In one embodiment as shown in FIGS. 5A and 5B, the sample vessel 300 resembles a thin disk. The sample vessel 300 includes a bottom portion or body 305, and a top portion or cap 310. A bottom region 315 of a sample holding well 318 of the body 305 and a top region 320 of a well cap 322 of the cap 310 are thin-walled as they will generally serve as the primary areas for contact with the thermoelectric modules for heat transfer to and from the sample within the vessel. The thin-walled portions 315 and 320 of the vessel may have a wall thickness between about 20 μm and about 300 μm. The body 305 and the cap 310 are preferably joined by an integrated living hinge 335 as well known in the art of thermoplastic fabrication. Through appropriate dimensional considerations of the body well 318 outer wall 340 diameter and cap well inner wall 345 diameter, a snap-fit of the cap 310 onto the bottom portion or body 305 may be achieved in conventional manner. Alternatively, any similarly tight seal or friction fit, such as an unhinged screwable or internally threaded cap and an externally threaded bottom well may be employed in the sample vessel of the present invention. In embodiments of the invention, tabs may be present on the edges of the cap and bottom components to facilitate manual assembly and de-assembly of the body and cap. In the open configuration, as shown in FIG. 5A, the sample mixture may be loaded or unloaded easily by standard pipetting techniques. The sample vessel may be closed by moving the hinged cap 310 into position of engagement with the bottom or body 305 as illustrated in FIG. 5B. In the closed configuration, the internal volume formed by the cap well 322 and the bottom well 318 preferably closely matches that of the sample mixture so that substantial contact (wetting) of the sample fluid with both circular regions 315 and 320 is achieved. In this embodiment, the height of the disk may remain fixed while the diameters of the wells may be varied to accommodate different reaction volumes.

Figure 6B:
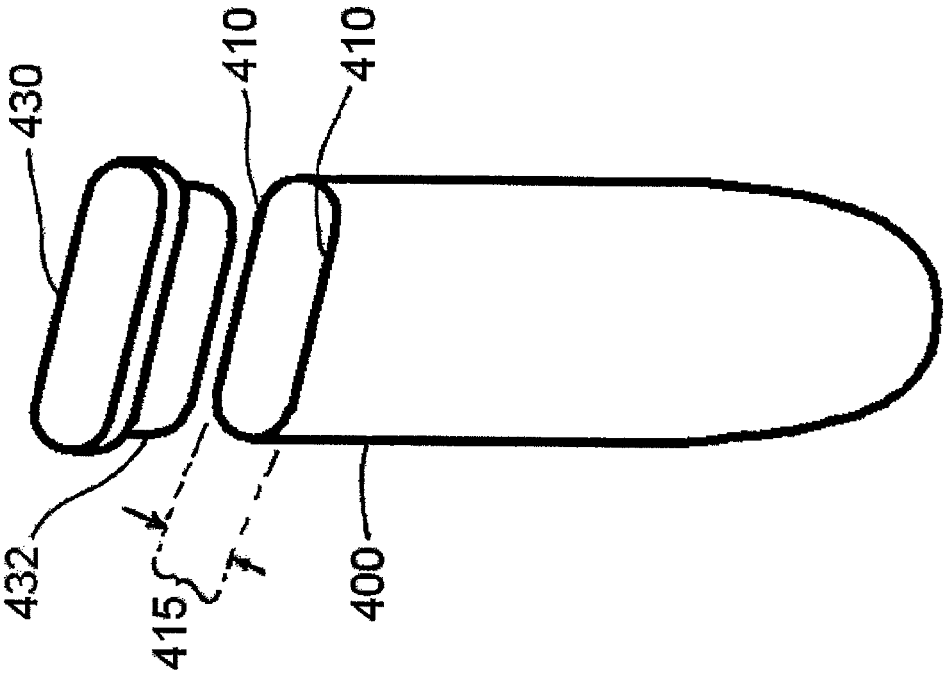
FIG. 6B is a perspective view of a flattened shape or flat oval rod embodiment of the deformable sample vessel of FIG. 6A.
Figure 6A:
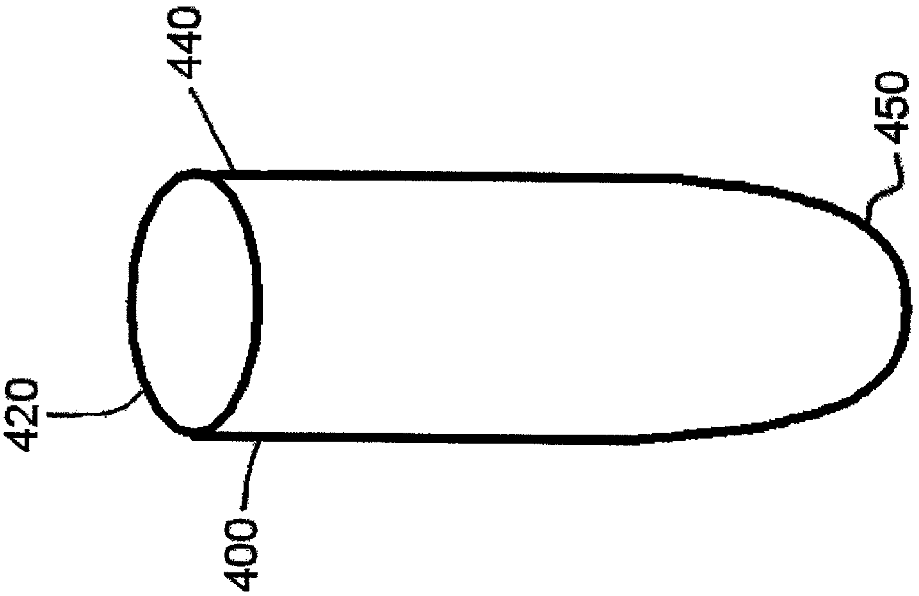
FIG. 6A is a perspective view of a potentially round configuration made from a deformable sample vessel of the present invention.

In another embodiment, the sample vessel may be deformable between a filling and emptying configuration and a PCR reaction or thermocycling configuration as shown in FIGS. 6A and 6B, respectively. As shown in FIGS. 6A and 6B the sample vessel may resemble a deformable cylinder. The vessel 400 is shown in both a potentially round configuration in FIG. 6A and a flattened shape in FIG. 6B. The two opposing flat sides 410 of the vessel 400 are separated by a small internal dimension 415 across its lumen to facilitate rapid thermocycling. In embodiments of the invention the vessel 400 may be fabricated from glass with a fixed flat oval shape as in FIG. 6B, or thin-walled plastic (such as but not limited to polypropylene) or metal (such as but not limited to aluminum) whereby the vessel walls may be deformable. In preferred embodiments, the vessel may be made from a resilient plastic so that after deformation it returns to its original shape. The shape of the vessel 400 need not be necessarily constant. In its native state, the vessel 400 may have a larger opening 420 (e.g. take on a more of a circular shape) as shown in FIG. 6A to allow for facile pipetting of the reaction mixture. When inserted into the thermocycler unit (such as in the slot 155 shown in FIG. 3), the vessel 400 of FIG. 6A is flattened on the sides and assumes an approximately flat oval rod to conform to the shape of the internal cavity or slot 155. The deformability and thin vessel walls also ensure that very good contact with the heat transfer surfaces of the thermoelectric modules of the thermocycler apparatus is made for rapid heat transfer. In a preferred embodiment, a cap 430 having a plug or protrusion 432 which fits into the mouth or top 410 of the vessel 400 as shown in FIG. 6B may be employed to seal the top of the vessel 400 after sample loading.

In alternative embodiments a cap without a plug may snap over the outer periphery of the vessel 400 or a sealing film could be employed. In embodiments of the invention, the cap may be attached to the body of the vessel by a flexible strip or hinge and which sealingly snaps onto the mouth or top 410 of the vessel 400 when the body is in a flattened or cycling configuration. The top neck portion 440 of the vessel 400 may also be expanded to aid in the loading of the sample. At the bottom end 450 or end opposite the opening for sample loading, the reaction vessel may be closed either during fabrication, using a bonded sealing film, or by heat crimping techniques as well known in the art. In a preferred embodiment, the vessel 400 may be fabricated by thermoforming techniques such that the sealed end 450 is optically transparent for on-line optics detection. It is useful to imagine a very short plastic straw that is sealed on one end. The sample mixture is loaded and the top sealed in a similar crimping fashion, or by a cap or sealing film. The vessel is then inserted into the slot in the cycling assembly (such as in the slot 155 shown in FIG. 3), where it deforms substantially into a flat oval shape with a very small distance across the lumen of the vessel. Temperature cycling is performed and then the vessel is removed where it substantially regains its original shape for sample mixture removal.

Figure 7B:
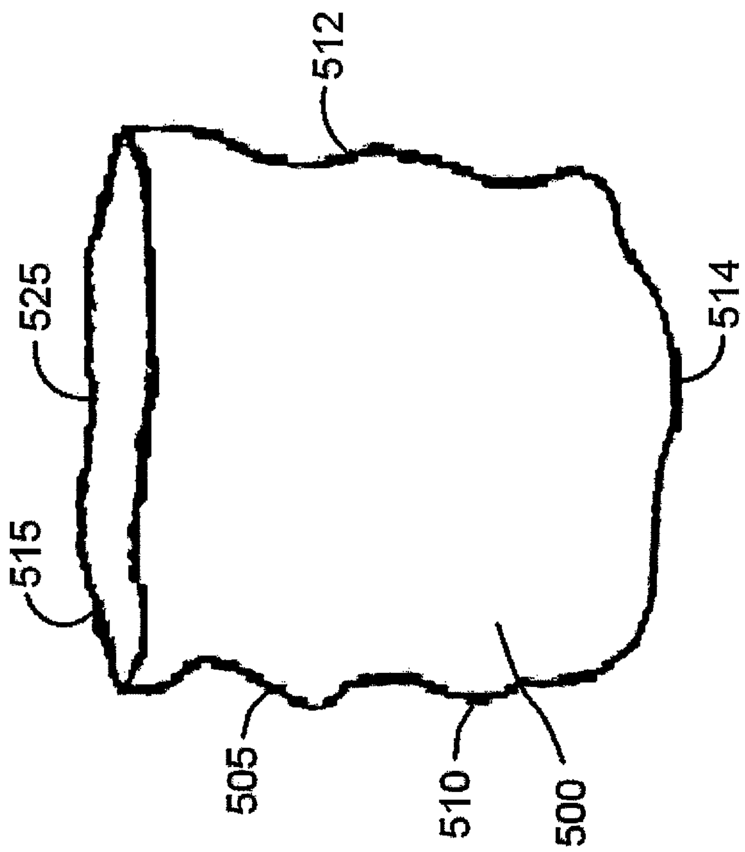
FIG. 7B is a perspective view of the thin film, deformable sample vessel of FIG. 7B which is deformed into a thinner shape for conforming to the sample cavity or space between the thermoelectric modules of the cycler of the present invention.
Figure 7A:
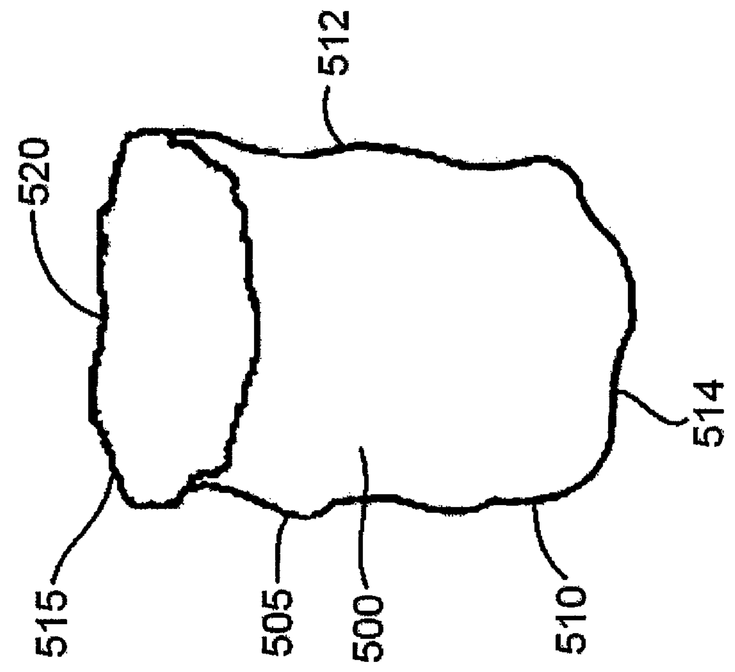
FIG. 7A is a perspective view of a thin film, deformable embodiment of the sample vessel of the present invention in a shape having a wide mouth to facilitate filling and removing of sample fluids from the vessel.

In another embodiment of a deformable sample vessel, the vessel 500 may be a thin film container, such as a plastic bag having a rectangular shape or any other shape, which may be regular or irregular as shown in FIGS. 7A and 7B. The vessel walls 505 may be comprised of thin films of thermoplastic material. The side edges 510, 512 and bottom edge 514 may bonded together by heat sealing techniques as well known in the art. The thinness of the film enables the vessel 500 to be easily manipulated into almost any desired shape. One edge, or the top edge 515 of the vessel 500 is not initially closed to allow for sample loading, but may be sealed by heat or simply clamped after sample loading. Upon completion of PCR, the seal may be broken or clamp removed to allow for sample removal. As shown in FIG. 7A the thin film, deformable sample vessel 500 may have a shape which provides a wide mouth 520 to facilitate filling and removing of sample fluids from the vessel 500. The wide mouth shape may be obtained by deforming the vessel or bag by squeezing or pinching the opposing sides 510 and 512 towards each other. As shown in FIG. 7B the thin film, deformable sample vessel 500 may be deformed into a thinner shape with a thin opening or mouth 525 for sealing of the top edge 515. The deformation into the thinner shape may be achieved by pulling the opposing sides 510 and 512 away from each other for conforming to the sample cavity or space between the thermoelectric modules of the cycler. The thin film container embodiments allow for extremely thin films to be used, for example on the order of tens of micrometers, which allows for rapid heat transfer. When this deformable vessel is placed into a thermocycler of the present invention, such as the hinged cycling assembly shown in FIG. 4, the vessel 500 conforms to the interior 280 of the thermocycler with a small dimension normal to the primary heat transfer or inside surfaces of the inner substrates 285, 290 of the thermocycler when in the closed position.

The above described representative embodiments and following examples are meant to serve as illustrations of the present invention, and should not be construed as a limitation thereof. A thermocycler apparatus or system as schematically shown in FIG. 1, may be assembled using conventional components employed in thermocycler apparatus. A thermocycler apparatus or system employed to conduct rapid PCR amplifications in the Examples of the present invention includes an AC/DC power supply obtained from TRC Electronics (Lodi, N.J.) and an H-bridge amplifier (part #FTA-600) obtained from Ferrotec USA (Nashua, N.H.). To control the H-bridge and receive thermocouple signals, a KUSB-3108 data acquisition module obtained from Keithley Instruments (Cleveland, Ohio) is employed. The controller has the capability to read thermocouples, provide cold junction compensation, and provide digital outputs for controlling the H-bridge amplifier. Software developed using Visual Basic is employed to program and execute the thermocycling of the apparatus.

Within the cycling assembly as schematically shown in FIG. 2, a fast response thermocouple (part #TJC36-CPSS-020U-6) from Omega Engineering Incorporated (Stamford, Conn.) is used. Two aluminum heat sinks (Aavid Thermalloy part #62500, 4 inch length) obtained from Scott Electronics (Lincoln, Nebr.) along with thermal paste are assembled with two thermoelectric modules (part #9500/127/085B) obtained from Ferrotec USA (Nashua, N.H.). The interior machined material components are fabricated at Precision Machine Company (Lincoln, Nebr.) out of aluminum. In Examples 1 and 2, the interior block is a 40×40×2.25 mm block with about 1.58 mm holes to accept glass capillaries as shown in FIG. 2. In Examples 3 and 4, a U-shaped aluminum piece with 1 mm thickness is used to create a slot between the thermoelectric modules as shown in FIG. 3. Thermal paste is used on all mating surfaces, and the parts are assembled via four bolts connecting the heat sinks near the corners. A radial DC fan (part #592-0930) from Allied Electronics (Fort Worth, Tex.) is used to provide forced air convection over the heat sinks.

The present invention is further illustrated in the following examples of rapid PCR amplifications performed using the thermocycler apparatus or system of the present invention, where all parts, ratios, and percentages are by weight, all temperatures are in degrees Celsius, all pressures are atmospheric unless otherwise stated, and the time 0 sec refers to a temperature protocol with negligible time that is spent at that temperature (eg. denaturation at 94° C. for 0 sec refers to rapid heating of the PCR sample to 94° C. followed by an immediate cooling to the next temperature set point with negligible amount of time spent at 94° C.):

Example 1

Figure 8A:
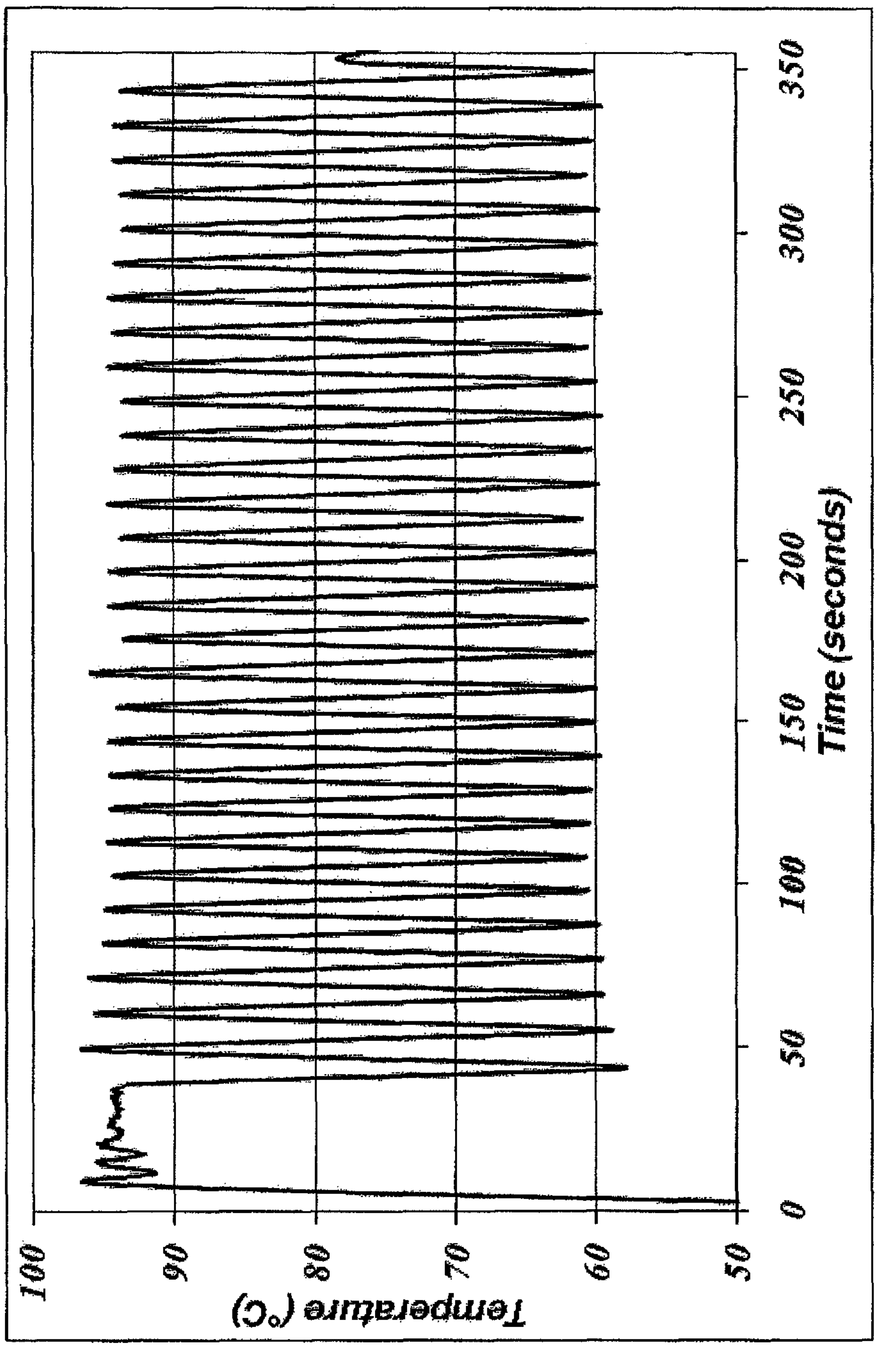
FIG. 8A illustrates a temperature versus time profile of a 355 second protocol for the DNA amplifications shown in FIG. 8B.
Figure 8B:
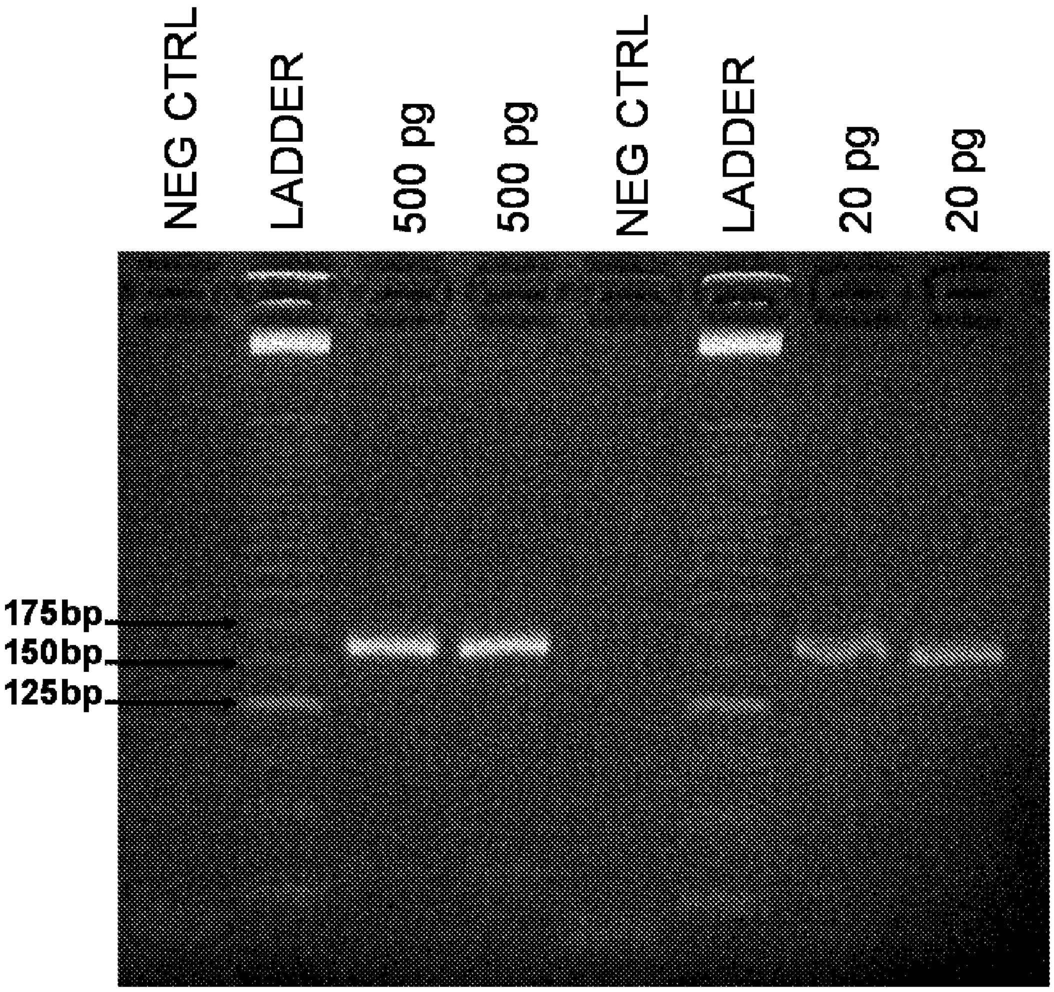
FIG. 8B is a picture of a gel electropherogram which shows amplification of 163 base pair DNA amplicons using glass capillaries in accordance with the present invention.

30 PCR Cycle Amplification of a 163 bp Product in 5:55 (355 Seconds) Using Glass Capillaries To demonstrate the rapid thermocycling of the invention, experiments were carried out in the thermocycler apparatus or system of the present invention to amplify a 163 bp product from lambda bacteriophage DNA (New England Biolabs) in thin-walled glass capillary tubes (Roche Applied Science). Each 25 μL reaction mixture consisted of 5 mM $MgSO_4$, 400 μg/ml BSA, 0.2 mM dNTPs, 0.7 μM each forward and reverse primers, 1×KOD reaction buffer, and 0.5 U of KOD Hot-Start-Polymerase (Novagen). Starting template DNA concentrations were either 500 pg or 20 pg, while negative controls were absent of starting template. Samples were processed in two separate runs (two 500 pg samples along with negative control ran simultaneously, two 20 pg samples with negative control run simultaneously). The cycling assembly used is illustrated in FIG. 2. The thermocycler was programmed to conduct a 30 second hot-start at 94° C., followed by 30 cycles of [94° C. for 0 sec and 60° C. for 0 sec], and a final extension at 72° C. for 5 sec. The thermocouple was placed in a glass capillary filled with water. The temperature versus time profile of the protocol is shown in FIG. 8A. The total runtime for the protocol was 355 seconds. After amplification, reaction products were separated on a 3% agarose gel stained with EtBr using 6 μL each of the products and a 25 bp molecular weight reference ladder (Invitrogen). FIG. 8B shows the gel electrophoregram of the reaction products (L1-Negative control; L2-25 bp ladder; L3-500 pg #1; L4-500 pg #2; L5-Negative control; L6-25 bp ladder; L7-20 pg #1; L8-20 pg #2). After 30 PCR cycles, all of the reaction products had successful amplification of the 163 bp product, while control reactions were negative. The difference in band intensities between the 500 pg and 20 pg lanes is due to the starting template concentrations.

Example 2

Figure 9A:
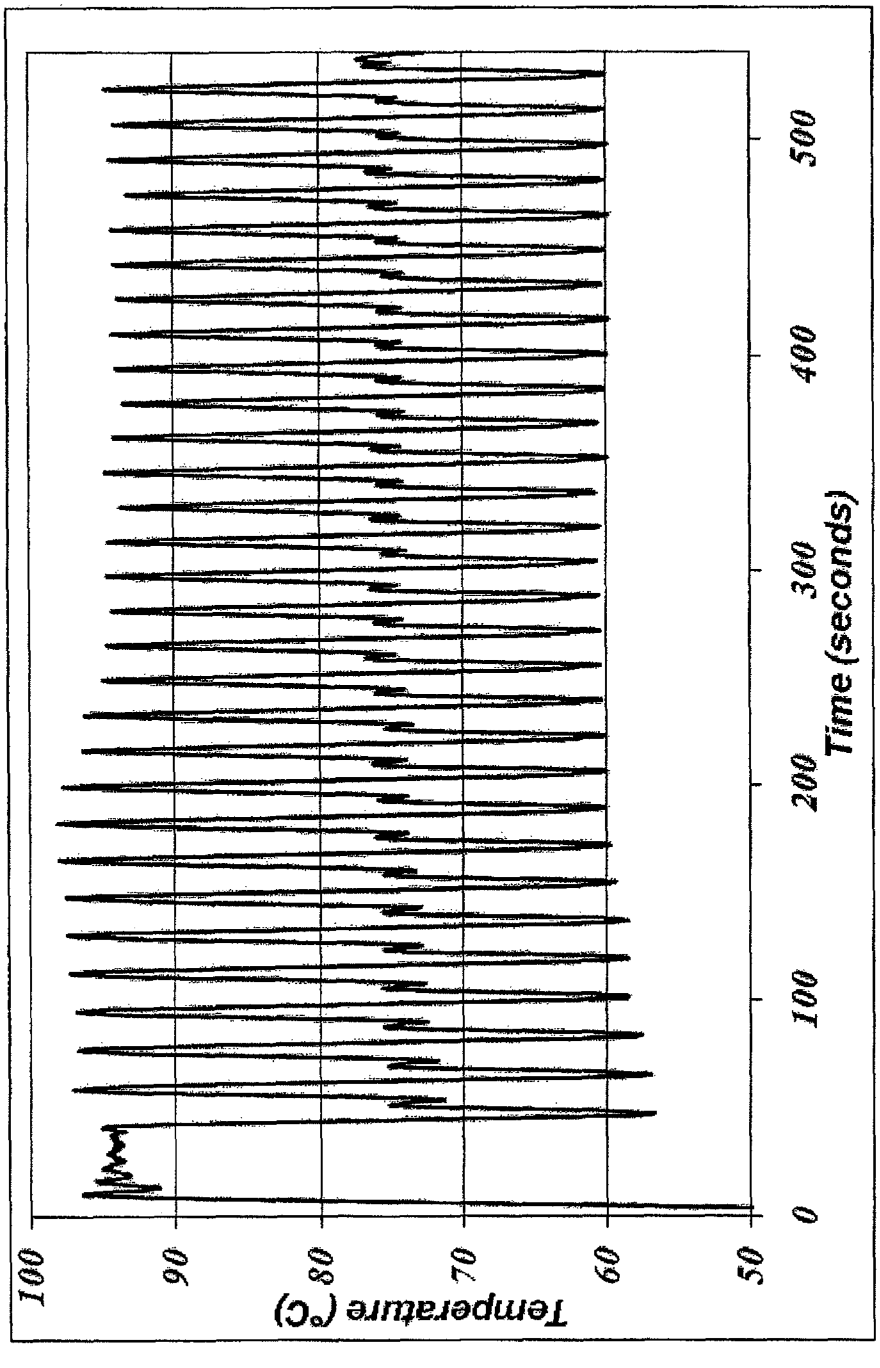
FIG. 9A illustrates a temperature versus time profile of a 538 second protocol for the DNA amplifications shown in FIG. 9B.
Figure 9B:
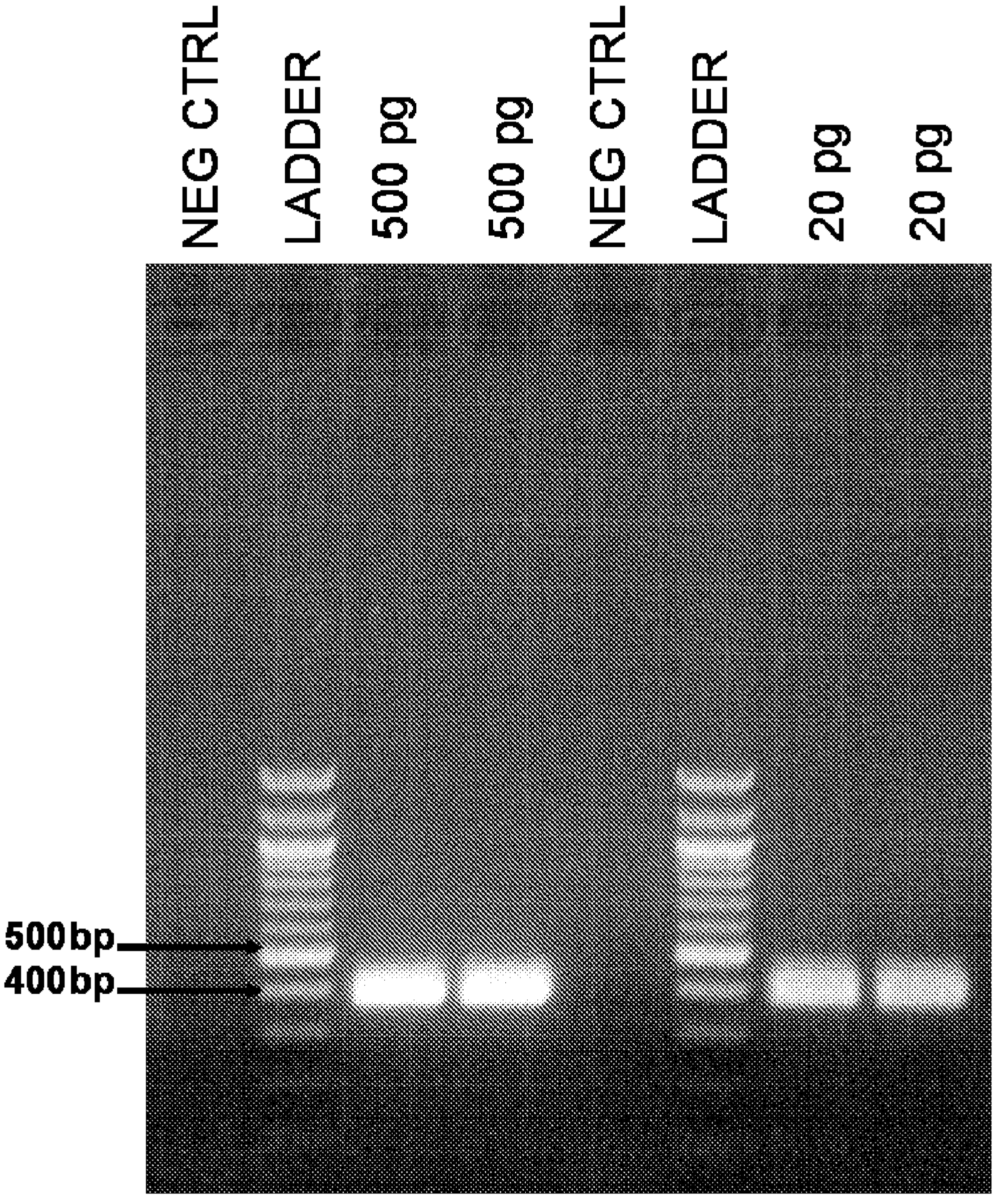
FIG. 9B is a picture of a gel electropherogram which shows amplification of 402 base pair DNA amplicons using glass capillaries in accordance with the present invention.

30 PCR Cycle Amplification of a 402 bp Product in 8:58 (538 Seconds) Using Glass Capillaries Experiments were carried out in the thermocycler apparatus or system of the present invention to amplify a longer 402 bp product from lambda bacteriophage DNA in thin-walled glass capillary tubes. The reaction composition was the same as in Example 1, except that different forward and reverse primers were used to generate the 402 bp product. A slightly more conservative protocol was run (30 second hot-start at 94° C., followed by 30 cycles of [94° C. for 2 sec, 60° C. for 2 sec, and 72° C. for 3 sec], and a final extension at 72° C. for 5 sec). The temperature versus time profile of the protocol is shown in FIG. 9A. The total runtime for the protocol was 538 seconds. After amplification, reaction products were separated on a 1% agarose gel stained with EtBr using 6 μL each of the products and a 100 bp molecular weight reference ladder (New England Biolabs). FIG. 9B shows the gel electrophoregram of the reaction products (L1-Negative control; L2-100 bp ladder; L3-500 pg #1; L4-500 pg #2; L5-Negative control; L6-100 bp ladder; L7-20 pg #1; L8-20 pg #2). Similar to Example 1, all of the reaction products had high yield of the desired 402 bp product, while control reactions were negative. Even with the hot-start and conservative hold times, the time to obtain high product yield was only 538 seconds.

Example 3

Figure 10A:
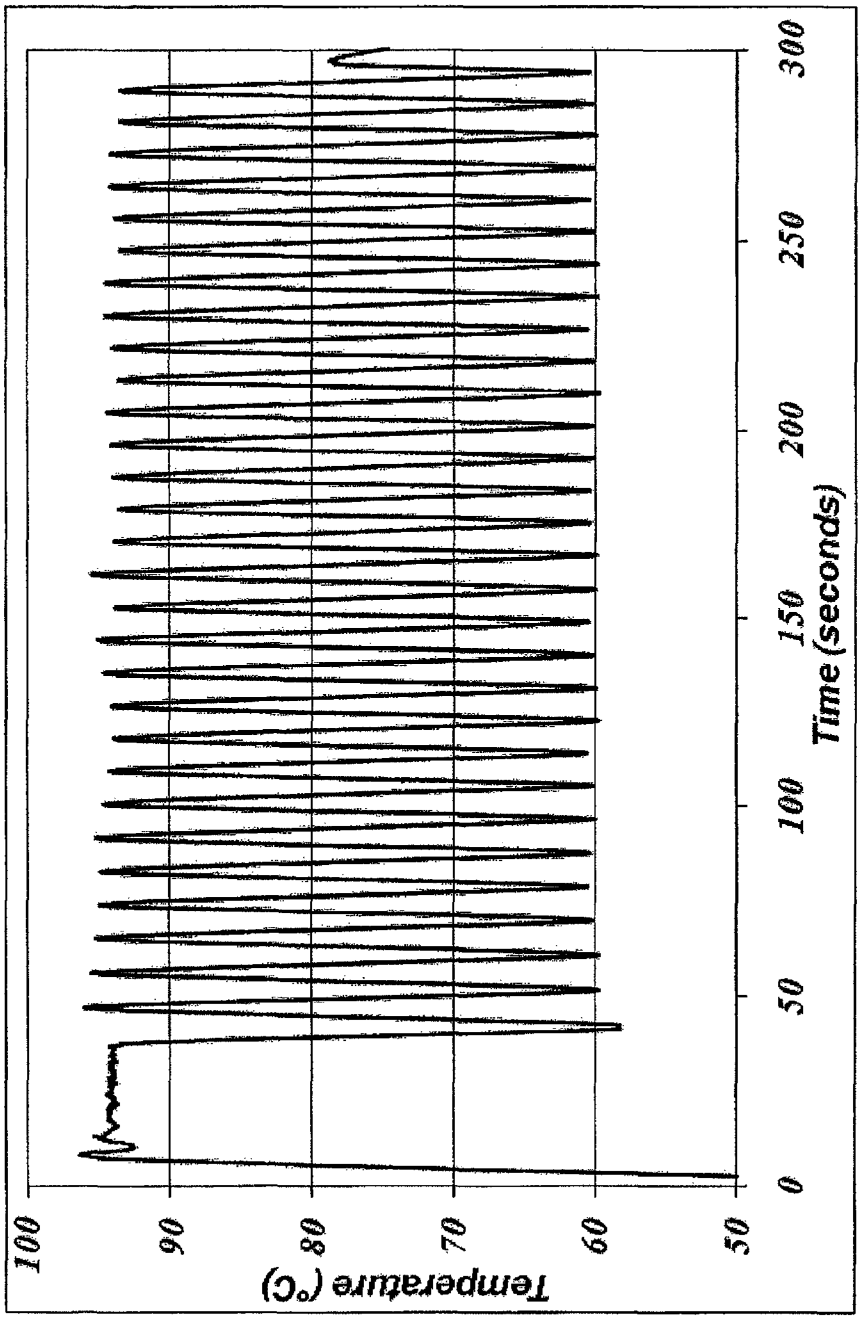
FIG. 10A illustrates a temperature versus time profile of a 300 second protocol for the DNA amplifications shown in FIG. 10B.
Figure 10B:
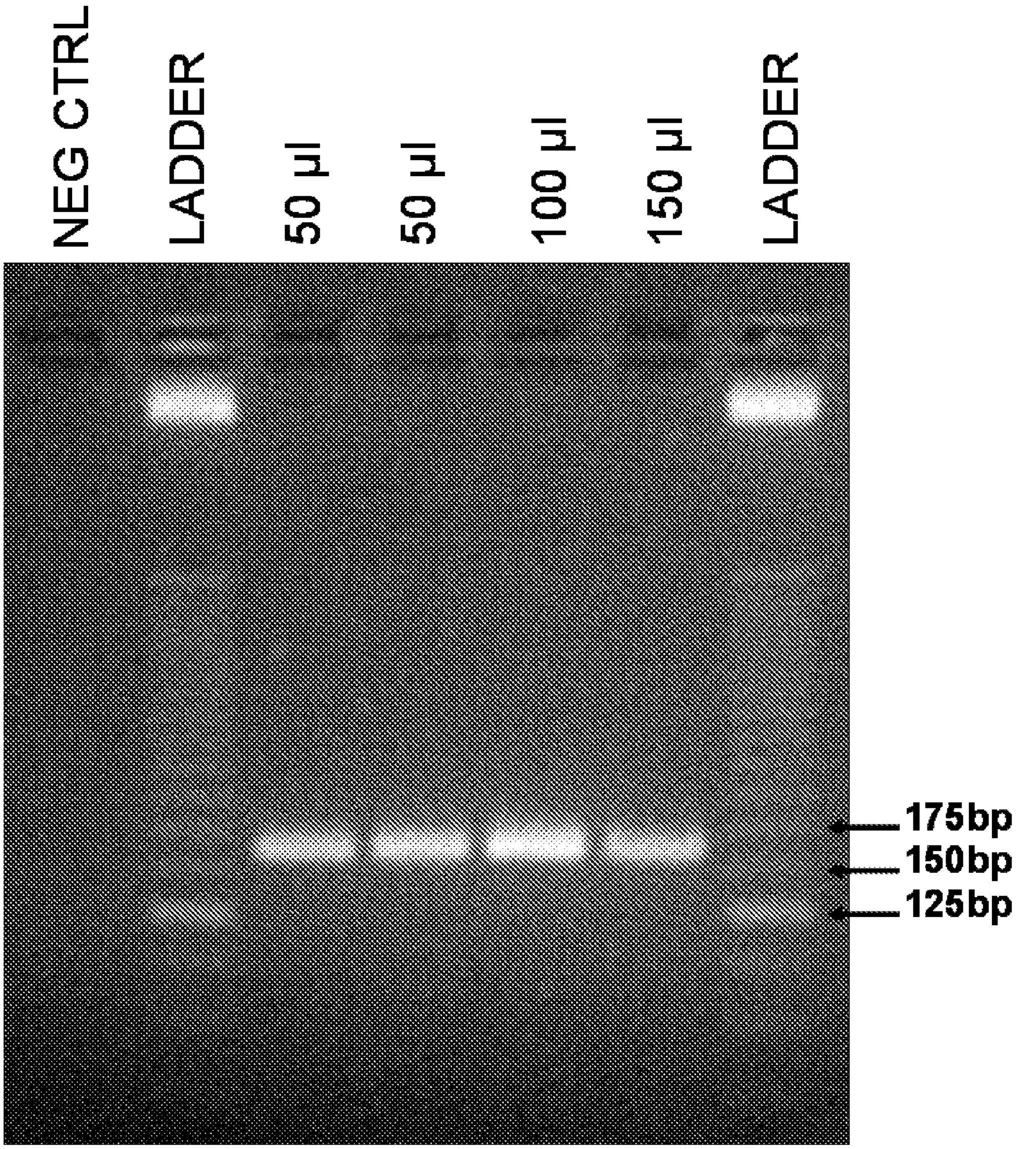
FIG. 10B is a picture of a gel electropherogram which shows amplification of 163 base pair DNA amplicons using plastic deformable cylinder vessels in accordance with the present invention.

30 PCR Cycle Amplification of a 163 bp Product in 5:00 (300 Seconds) Using Plastic Deformable Cylindrical Vessels In this example, a sample vessel as illustrated in FIG. 6 and slotted cycling assembly of FIG. 3 was used with a thermocycler apparatus or system of the present invention. The vessel was made out of polypropylene with a wall thickness of about 200 μm. In its native configuration, the vessel was approximately circular in cross section with a diameter of about 8 mm. When inserted into the 1 mm thermocycler slot, each vessel deformed into a flat oval rod with substantial contact with the inner substrates of the thermoelectric modules. The reaction composition was the same as Example 1 but without BSA: 5 mM $MgSO_4$, 0.2 mM dNTPs, 0.7 µM each forward and reverse primers, 1×KOD reaction buffer, and 0.5 U of KOD Hot-Start-Polymerase. The starting template amount per sample was 500 picograms. Reaction volumes were 50 µL (negative control), 50 µL, 50 µL, 100 µL, and 150 µL. Multiple samples were processed within the same run. The same protocol as in Example 1 was used: 30 second hot-start at 94° C., followed by 30 cycles of [94° C. for 0 sec and 60° C. for 0 sec], and a final extension at 72° C. for 5 sec. The thermocouple was placed in a sample vessel filled with water. The temperature versus time profile of the protocol is shown in FIG. 10A. The total runtime for the protocol was about 300 seconds, faster than that achieved with glass capillaries. After amplification, reaction products were separated on a 3% agarose gel stained with EtBr using 8 µL each of the products and a 25 bp molecular weight reference ladder. FIG. 10B shows the gel electrophoregram of the reaction products (L1-Negative control; L2-25 bp ladder; L3-50 µL; L4-50 µL; L5-100 µL; L6-150 µL; L7-25 bp ladder).

Example 4

Figure 11A:
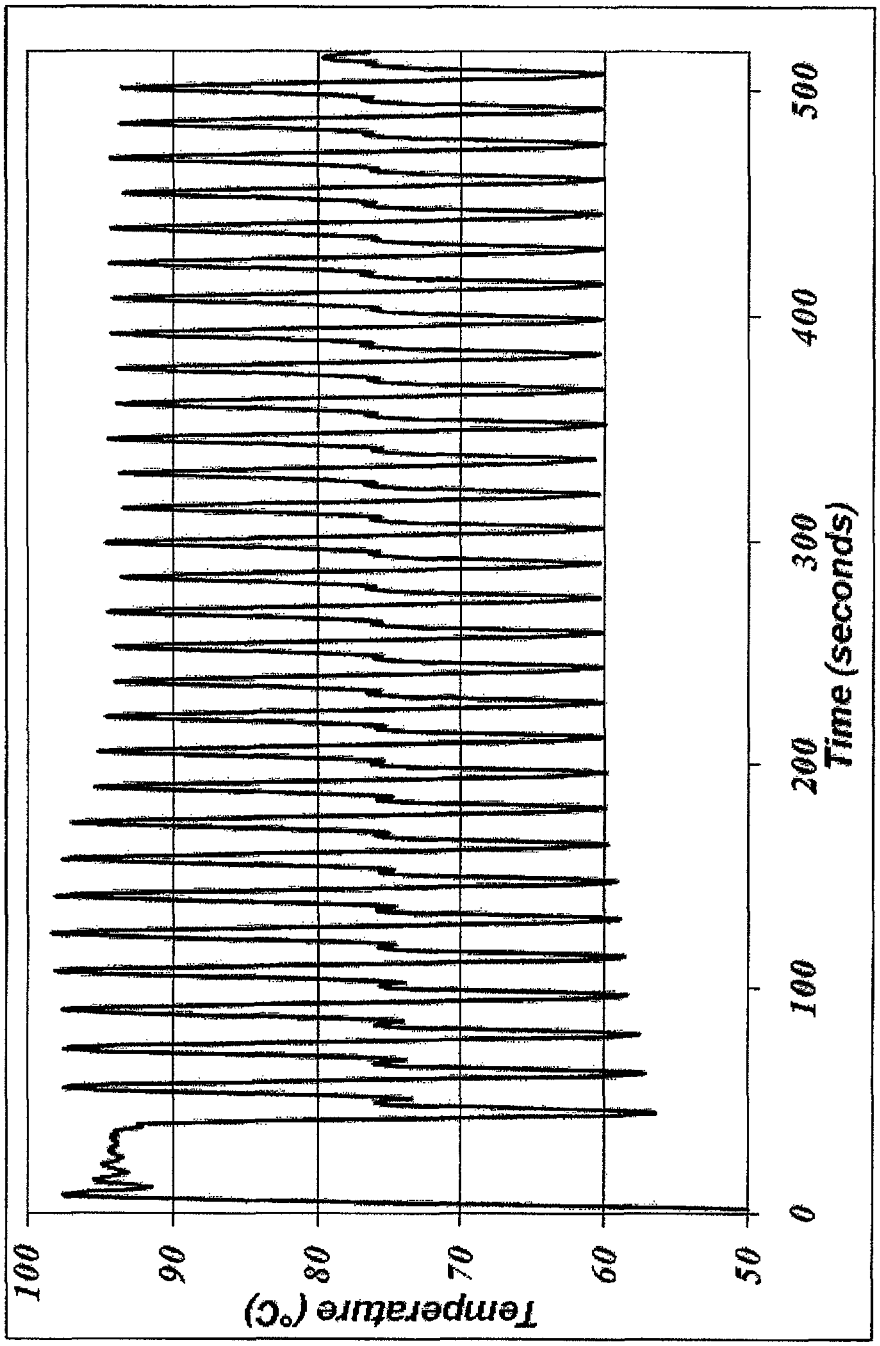
FIG. 11A illustrates a temperature versus time profile of a 517 second protocol for the DNA amplifications shown in FIG. 11B.
Figure 11B:
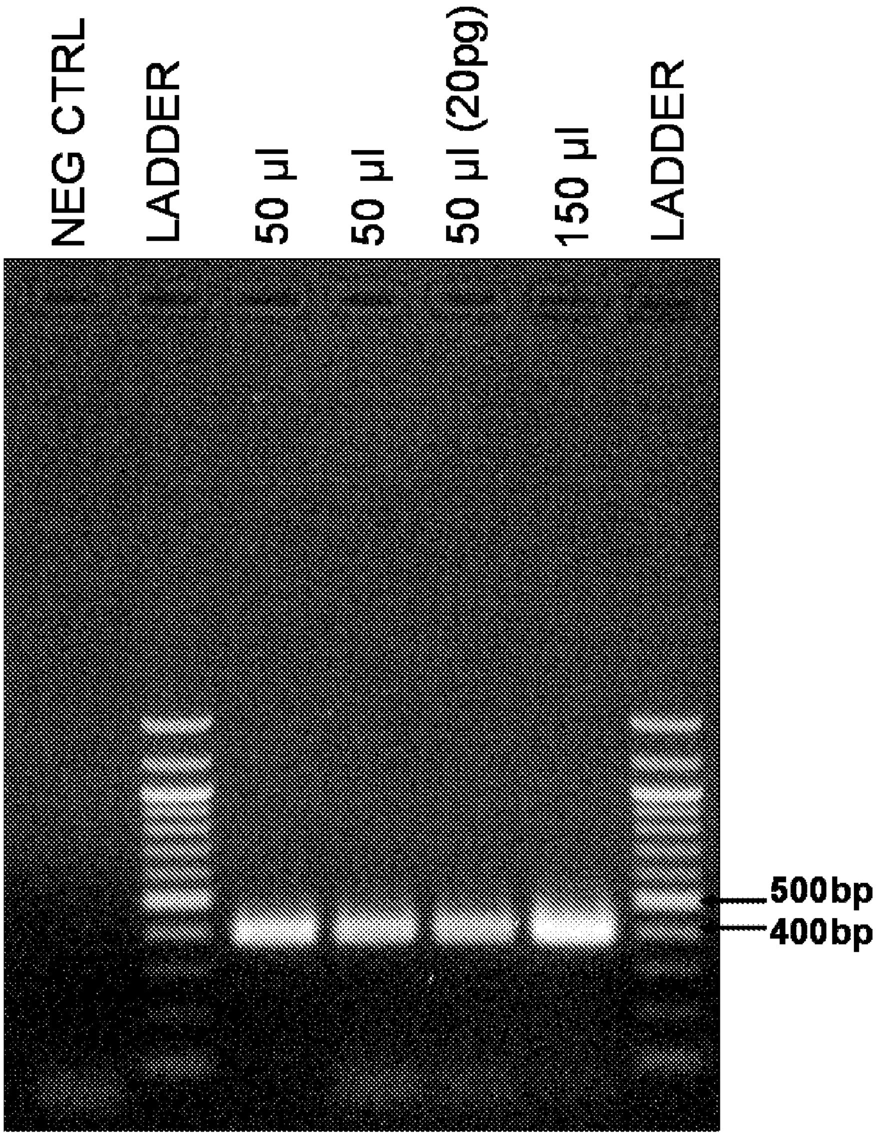
FIG. 11B is a picture of a gel electropherogram which shows amplification of 402 base pair DNA amplicons using plastic deformable cylinder vessels in accordance with the present invention.

30 PCR Cycle Amplification of a 402 bp Product in 8:37 (517 Seconds) Using Plastic Deformable Cylindrical Vessels As in Example 3, the plastic deformable vessels of FIG. 6 and slotted cycling assembly of FIG. 3 were utilized with a thermocycler apparatus or system of the present invention. The reaction composition (less BSA) and primers from Example 2 were employed to amplify a 402 bp product from lambda bacteriophage DNA. The starting template amount per sample was 500 pg (one sample at 20 pg). Reaction volumes were 50 µL (negative control), 50 µL, 50 µL, 50 µL (20 pg template), and 150 µL. Multiple samples were processed within the same run. The PCR protocol was: (30 second hot-start at 94° C., followed by 30 cycles of [94° C. for 2 sec, 60° C. 2 sec, and 72° C. for 3 sec], and a final extension at 72° C. for 5 sec). A temperature versus time profile of the protocol is shown in FIG. 11A. The total runtime for the protocol was about 517 seconds. After amplification, reaction products were separated on a 1% agarose gel stained with EtBr using 8 µL each of the products and a 100 bp molecular weight reference ladder (New England Biolabs). FIG. 11B shows the gel electrophoregram of the reaction products (L1-50 µL negative control; L2-100 bp ladder; L3-50 µL; L4-50 µL; L5-50 µL with 20 pg template; L6-L150 µL; L7-100 bp ladder).

The preceding examples clearly demonstrate the performance of the present invention. Unlike any other Peltier-based thermocycler, the present invention can amplify products in high yield through 30 PCR cycles in five to ten minutes. The correct length product was amplified in all cases, as evidenced by the respective gel electropherograms of the PCR products while control reactions were negative for DNA amplification.

Temperature ramp rates for both heating and cooling in Examples 1, 2, 3, and 4 averaged 7° C./sec, regardless of sample volume which ranged from 25 µL to 150 µL. Temperature ramp rates are defined here as the absolute value of the rate in which the actual temperature of the PCR sample changes during the heating or the cooling phase as measured by a fast-response thermocouple. Temperature ramp rates for heating and cooling were comparable but are not necessarily equal. Temperature ramp rates do vary with the current sample temperature and generally range between 5° C./sec and 15° C./sec. Temperature ramp rates of the sample vessel holder and of the thermoelectric modules greatly exceed the temperature ramp rates of the center of the PCR sample, and these devices heat or cool at a rate generally exceeding 15° C./sec.

A key advantage of the present invention is the processing of larger reaction volumes without substantial increases in cycling times. The present invention permits the use of large sample volumes, for example from about 104, to about 250 µL or more, with short cycling times, for example from about 2 seconds to about 20 seconds. In particularly advantageous embodiments of the present invention, samples sizes of at least about 25 µL preferably at least about 50 µL, for example from about 100 µL to about 250 µL can be employed with cycle times of from about 2 seconds to about 20 seconds. Conducting PCR on larger sample volumes is highly beneficial for diagnostic applications where sensitivity is important. This is epitomized in Example 3 and Example 4, where 150 µL reaction volumes were employed.

In Example 3, one PCR cycle spanning from 94° C. to 60° C. was completed in about 9 seconds, faster than any other known Peltier-based thermocycler and especially with larger volumes. While a short 163 bp product was amplified, the amplification of longer products only requires a hold at about the optimal polymerase extension (usually 72° C.). Thus, the cycling times for longer products will depend on the rate of polymerase extension. In the case of KOD polymerase, the extension rate is 100-130 nucleotides per second. To amplify a 1000 base pair product, roughly 8 seconds of hold time would generally be added, yielding 17 seconds per cycle. Also, adjustments to the denaturation and annealing temperatures can be employed as well as enzymes with higher extension rates. Even with about 1000 base pair amplification products, the present invention is easily capable of completing a PCR cycle spanning generally employed temperature ranges in under 20 seconds.

In embodiments of the invention, the temperature of the contents of a sample vessel may be cycled between a low temperature range of about 55° C. to about 72° C. and a high temperature range of about 85° C. to about 98° C. and back to the low temperature range in a time frame of about 2 seconds to about 20 seconds per cycle. In exemplary embodiments of the invention, the temperature of the contents of a sample vessel may be cycled to synthesize copies of DNA of from about 50 to about 1,000 nucleic acid base pairs in length by the polymerase chain reaction. These cycling temperatures and times, and synthesis of base pair copies may be achieved using a thermocycler with a plurality of thermocycler modules and a sample vessel having an internal volume which can hold sample contents of from about 10 µL to about 250 µL or more, preferably from about 50 µL to about 250 µL.

The addition of on-line optical detection can be implemented in the apparatus to combine rapid PCR thermocycling with real-time product detection. The present invention has great utility due to its speed, robust solid-state design, and capacity to handle any number of samples and reaction volumes. In addition to PCR, the present invention may be used for other applications which require fast and controlled temperature cycling of samples.

A general description of the present invention as well as preferred embodiments has been set forth above. The present invention may be embodied in other specific forms without departing from its spirit or essential characteristics. Those skilled in the art will recognize and be able to practice additional variations in the methods and devices described which fall within the teachings of this invention. Accordingly, all such modifications and additions are deemed to be within the scope of the invention which is to be limited only by the claims appended hereto.

What is claimed is:

1. A thermocycler for subjecting one or a plurality of samples to rapid thermal cycling comprising:
at least one pair of thermoelectric modules, each module in direct contact with a heat sink and each module having an interior module face for heating and cooling one or a plurality of sample vessels each containing a sample;
wherein the thermoelectric modules of each pair are positioned such that:
the module faces of the thermoelectric module pair are in substantial opposition to each other with an interior solid silver sample holder in direct contact with and in between the opposing module faces for receiving said one or a plurality of sample vessels; and
a controller electrically connected to each pair of thermoelectric modifies for regulating the temperature so that any sample vessels placed within the sample holder experience uniform temperature cyclings;
wherein the sample holder includes one or more oval openings for receiving the sample vessel, each opening having a shape so that the sample vessel is deformed to an oval shape upon entry into the sample holder openings
wherein the thermoelectric modules are the only provided sources of heating the vessels so that uniform temperature is maintained by the direct contact between the thermoelectric devices and solid sample block; and
wherein the distance between inner surfaces of the sample vessels in a direction perpendicular to a surfaces of the module faces is less than 2.5 mm.

2. A thermocycler as claimed in claim 1, wherein the thermoelectric modules of each pair are positioned such that the module faces of each thermoelectric module pair are in substantial opposition such that the semiconductor elements in the opposing modules are separated by a distance of out 0.5 mm to about 10.0 mm.

3. The thermocycler of claim 1, wherein the sample vessel includes a polypropylene material.

4. The thermocycler of claim 1, wherein the sample holder includes a sensor in which the voltage or resistance signal changes with temperature to measure the temperature within the sample holder.

5. The thermocycler of claim 1, which is capable of amplifying an about 163 base pair sample located within the deformable sample vessel when subjected to 30 amplification cycles in about 300 seconds as analyzed by gel electrophoresis.

6. The thermocycler of claim 1, which is capable of amplifying an about 402 base pair sample located within the deformable sample vessel when subjected to 30 amplification cycles in about 517 seconds as analyzed by gel electrophoresis.

7. The thermocycler of claim 1, which is capable of processing a sample of from about 25 μl to about 250 μl is amplified by the thermocycler in cycle times of about 2 seconds to about 20 seconds and provides accurate gel electrophoresis results for the product amplified.

8. The thermocycler of claim 1, which is capable of processing a sample of about 100 μl through a PCR cycle spanning 94° C. to 60° C. in about 9 seconds.

9. The thermocycler of claim 1, wherein the sample vessel can hold contents of about 10 μl to about 250 μl in volume, the temperature of a sample can be varied between a low temperature range of about 55° C. to about 72° C. and a high temperature range of about 85° C. to about 98° C. and back to the low temperature range in a time frame of from about 2 seconds to about 20 seconds per cycle.

10. The thermocycler of claim 1, wherein the sample vessel is substantially deformable between a first sample filling shape prior to insertion into the sample holder and a second rapid thermocycling shape after insertion into the sample holder.

11. The thermocycler of claim 1, wherein the thermoelectric modules are hinged together at one end for insertion and removal of sample vessels from the sample holder when the hinge is opened, and thermocycling when the hinge is closed.

12. The thermocycler of claim 1, including at leas pairs of thermoelectric modules, wherein the controller controls the pairs of thermoelectric modules so that the modules run independent temperature protocols simultaneously.

13. The thermocycler of claim 1, wherein the thermoelectric modules are positioned such that the module faces of each thermoelectric module pair are in substantial opposition such that semiconductor elements in the opposing modules are separated by a distance of about 0.5 mm to about 10.0 mm.

14. A thermocycler for subjecting one or a plurality of samples to rapid thermal cycling comprising:
a heat source consisting essentially of at least one pair of thermoelectric modules each having an interior module face in direct contact with a heat sink and a sample holder for heating and cooling one or a plurality of sample vessels each containing a sample and located within the sample holder;
wherein the thermoelectric modules of each pair are positioned so that:
the module faces of the thermoelectric module pair are in substantial opposition to each other with the sample holder composed of a solid silver material having a high thermal conductivity but low thermal mass between the opposing module faces for receiving said one or a plurality of sample vessels, and;
a controller electrically connected to each pair of thermoelectric modules for regulating the temperature so that any sample vessels placed within the sample holder experience uniform temperature cycling.

15. The thermocycler of claim 14, wherein the temperature within the sample holder is cycled between a low temperature range of about 55° C. to about 72° C. and a high temperature range of about 85° C. to about 98° C. and back to the low temperature range in a time frame of from about 2 seconds to about 20 seconds per cycle.

16. The thermocycler of claim 14, which is capable of amplifying an about 163 base pair sample located within the deformable sample vessel when subjected to 30 amplification cycles in about 300 seconds as analyzed by gel electrophoresis.

17. The thermocycler of claim 14, which is capable of amplifying an about 402 base pair sample located within the deformable sample vessel when subjected to 30 amplification cycles in about 517 seconds as analyzed by gel electrophoresis.

18. The thermocycler of claim 14, which is capable of processing a sample of from about 25 μl to about 250 μl is amplified by the thermocycler in cycle times of about 2 seconds to about 20 seconds and provides accurate gel electrophoresis results for the product amplified.

19. The thermocycler of claim 14, which is capable of processing a sample of about 100 μl through a PCR cycle spanning 94° C. to 60° C. in about 9 seconds.

20. The thermocycler of claim 14, wherein the sample holder includes a silver material and the sample vessel is a glass capillary.

21. The thermocycler of claim 14, wherein the sample vessel can hold contents of about 10 μl to about 250 μl in volume, the temperature of a sample can be varied between a low temperature range of about 55° C. to about 72° C. and a high temperature range of about 85° C. to about 98° C. and back to the low temperature range in a time frame of from about 2 seconds to about 20 seconds per cycle.

22. The thermocycler of claim 14, wherein the sample vessel is resilient forming a first shape prior to insertion into the sample holder, a second shape after insertion into the sample holder, and returning to substantially the first shape after removal from the sample holder.

23. The thermocycler of claim 14, wherein the thermoelectric modules are hinged together at one end for insertion and removal of sample vessels from the sample holder when the hinge is opened, and thermocycling when the hinge is closed.

24. The thermocycler of any claim 14, including at least two pairs of thermoelectric modules, wherein the controller controls the pairs of thermoelectric modules so that the modules run independent temperature protocols simultaneously.

* * * * *

UNITED STATES PATENT AND TRADEMARK OFFICE

CERTIFICATE OF CORRECTION

PATENT NO. : 9,034,635 B2
APPLICATION NO. : 12/918594
DATED : May 19, 2015
INVENTOR(S) : Joel R. Termaat It is certified that error appears in the above-identified patent and that said Letters Patent is hereby corrected as shown below:

In the Claims

Column 18, Line 12, Claim 12 “leas” should be “least”

Signed and Sealed this
Eighth Day of September, 2015

Michelle K. Lee
*Director of the United States Patent and Trademark Office*